US008241648B2

(12) United States Patent
Zhou et al.

(10) Patent No.: US 8,241,648 B2
(45) Date of Patent: Aug. 14, 2012

(54) AMPHIPHILIC OR LIPOPHILIC POLAR FUNCTIONALIZED FULLERENES AND THEIR USES

(75) Inventors: Zhiguo Zhou, Winston-Salem, NC (US);
Robert P. Lenk, Danville, VA (US);
Darren Macfarland, Danville, VA (US);
Kenneth L. Walker, Semora, NC (US);
Jing Zhang, Danville, VA (US);
Stephen R. Wilson, Danville, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 512 days.

(21) Appl. No.: 12/073,230

(22) Filed: Mar. 3, 2008

(65) Prior Publication Data

US 2008/0213324 A1    Sep. 4, 2008

Related U.S. Application Data

(60) Provisional application No. 60/904,401, filed on Mar. 2, 2007.

(51) Int. Cl.
*A61K 8/02* (2006.01)
*A61K 9/127* (2006.01)

(52) U.S. Cl. ..................... 424/401; 424/450
(58) Field of Classification Search .......... 424/401
See application file for complete search history.

(56) References Cited

U.S. PATENT DOCUMENTS

| 6,599,891 | B2 * | 7/2003 | North et al. ............ 514/183 |
| 7,238,367 | B2 | 7/2007 | Tardi et al. |
| 2005/0136079 | A1 * | 6/2005 | Burangulov et al. ...... 424/401 |
| 2007/0258329 | A1 * | 11/2007 | Winey .................. 367/140 |

FOREIGN PATENT DOCUMENTS

| WO | WO 2005/039535 A1 | 5/2005 |
| WO | WO 2007/043074 A1 | 4/2007 |

OTHER PUBLICATIONS

Connerade et al. (A Simple atomic model for hydrogen confined inside a prolate-shaped C60 fullerene cage), J. Phys. B: At. Mol. Opt. Phys. 34 (2001) 2505-2511.*
International Search Report (Form PCT/ISA/210) and the Written Opinion of the International Searching Authority (Form PCT/ISA/237) mailed Oct. 31, 2008 in corresponding International Application No. PCT/US2008/002789.

* cited by examiner

*Primary Examiner* — Sreeni Padmanabhan
*Assistant Examiner* — Timothy E Betton
(74) *Attorney, Agent, or Firm* — Albrecht Tousi & Farnum PLLC; Susan M. Dadio

(57) ABSTRACT

Described herein are synthetically modified fullerene molecules, wherein the fullerene is preferably ellipsoid in shape with an equatorial band and two opposing poles, comprising an adduct at one or both poles, at least one adduct being a hydrophobic chemical moiety capable of anchoring the fullerene on or in a lipid membrane.

17 Claims, 8 Drawing Sheets

AMPHIPHILIC OR LIPOPHILIC POLAR FUNCTIONALIZED FULLERENES AND THEIR USES

RELATED APPLICATION

This application claims priority of U.S. Application No. 60/904,401, filed Mar. 2, 2007, which is hereby incorporated by reference in its entirety for all purposes.

FIELD

The invention relates to synthetically modified fullerenes and their uses.

BACKGROUND

Fullerene derivatives have been proposed as free radical scavengers. See, e.g., U.S. Pat. No. 5,648,243 to Chiang. A number of academic investigations have studied water soluble $C_{60}$ derivatives as potential free radical anti-oxidant therapeutics. See, e.g., Jensen et al., *Bioorganic & Medicinal Chemistry,* 4:767-79, 1996; Da Ros et al., *Croatica Chemica Acta CCACAA* 74:743-55 (2001); and Wilson, in "Perspectives in Fullerene Nanotechnology," Osawa, ed., (Kluwer Academic Publishers, Dorcrecht, Netherlands, 2000); Syrensky, et al., *Kopf Carrier* #63, (David Kopf Instruments Tujunga, Calif., September 2006).

Chiang and colleagues used polyhydroxlated fullerenes to treat laboratory animals in models for ischemia/reperfusion injury, HIV infection, and for neuroprotection. Y. L. Lai and L. Y. Chiang, *J. Autonomic Pharmacol.,* 17:229, 1997; Schinazi et al., *Proc. Electrochem. Soc.,* 97:10, 1997; Lai et al., *World J. Surg.,* 24:450, 2000; Jin et al., *J. Neuroscience Res.,* 62:600, 2000; Huang et al., *Free Radical Biol. Med.,* 30:643, 2001.

Water soluble alkylsulfonyl fullerene derivatives have been shown to be effective in models of focal ischemia, and for photodynamic therapy. Chi et al., in "Perspectives of Fullerene Nanotechnology," pp 165-183, E. Osawa ed., (Kluwer Academic Publisher, Great Britain, 2002). A tris-malonate derivative, in which the malonate groups are oriented in an equatorial (eee) configuration, C3, has been demonstrated to be effective in preventing oxidative stress in cultured neurons. These observations were translated into efficacy in a model for amyotrophic lateral sclerosis. This same compound also prolonged the life span of mice fed C3 daily. Dugan et al., *P.N.A.S.* 94:9434-39, 1997; Dugan et al., *Parkinsonism & Related Disorders* 7:243-46, 2001; Quick et al., *Neurobiol of Aging* (electronic publication 2006).

Incorporation of fullerenes into lipid vesicles has been studied. Bensasson et al. (*Journal of Physical Chemistry,* 98:3492-3500, 1994) described preparing vesicles incorporating $C_{60}$ in L-α-phosphatidyl-choline purified from egg yolk (Egg-PC). However, the authors reported that they were not able to incorporate more than 3% by weight $C_{60}$ in Egg-PC liposomes and the preparation was not uniformly reproducible. Moreover, the preparation was not designed to be stable and would not have been suitable for administration as a pharmaceutical, diagnostic, cosmetic, or excipient composition.

Modification of fullerenes to produce vesicles has been reported. Hirsch et al. (*Angewandte Chemie International Edition,* 39:1845-1848, 1999) described $C_{60}$ to which six pairs of alkyl chains and one polar group was attached. See also U.S. Pat. No. 7,070,810. Felder et al., *Helv. Chim. Acta,* 85: 288-319, 2002, described a series of compounds wherein complex amphiphilic adducts are coupled to $C_{60}$. These compounds were designed to self assemble into monolayer films and could not readily be incorporated in biological membranes. Thus, these compounds would not be desirable for therapeutic biological applications.

Fullerenes, including many modified fullerenes that have been studied, have a tendency toward aggregation that can render a composition unsuitable for use as a therapeutic. For example, Williams et al., *Recueil des Travaux des Pays-Bas,* 1:72-6, 1996, incorporated $C_{60}$ into L-α-phosphatidyl-ethanolamine from *E. coli* (PE). Their procedure intentionally initiated formation of $C_{60}$ clusters, which the authors reported as essential for reproducible preparations. The authors further reported that incorporation of $C_{60}$ in PE was limited to 7% with $C_{60}$ adducts being limited to 3%. The limited incorporation means that these compositions are not desirable for use in vivo. Furthermore, the presence of clusters renders the compositions undesirable for use for in vivo delivery, because of the significant risk of toxicity and lack of uniformity.

Fullerenes are hydrophobic, and are generally not soluble in water, but also have poor solubility in lipids. See, e.g., Braun et al., *Fullerenes, Nanotubes and Carbon Nanostructures,* 15:311-314, 2007. Generally, $C_{60}$ and other fullerenes do not dissolve in lipids or in many common organic solvents (e.g. hexane, or chloroform).

Kato et al., *Chem & Biodiv.,* 2:1232-1241, 2005, describe $C_{60}$ with bis mannopyranosyl adducts. These structures are amphiphilic, but the hydrophobic moiety is the $C_{60}$ cage, which is not lipophilic. Hydrophobic forces cause the $C_{60}$ bis mannopyranosyl adducts to aggregate. Those aggregates are quite different from biological lipid membranes. The molecules did not associate with dipalmitoyl phosphatidyl choline phospholipid bilayers. Similar aggregation of $C_{60}$ porphyrin adducts has been described by Georgakilas et al, *Proc. Nat. Acad. Sci.,* 99:5075-5080, 2002. Such aggregates are not comparable or compatible with biological membranes.

Use of fullerenes as antioxidants, particularly in a therapeutic context, has not been adopted, primarily because of problems inherent in the fullerenes and problems in preparing a pharmaceutically acceptable composition and delivery system. Thus, there remains a need in the art for improved fullerene based antioxidants and appropriate delivery systems.

SUMMARY

Described herein are synthetically modified fullerene molecules, wherein the fullerene is spheroid or ellipsoid in shape with an equatorial band and two opposing poles, comprising an adduct at the opposing poles, at least one adduct being a lipophilic chemical moiety.

In an embodiment the fullerene molecule has the formula $$Z_m\text{—F—}Y_n;$$

wherein F is fullerene of formula $C_p$ or $X@C_p$, the fullerene having two opposing poles and an equatorial region;

Z and Y are positioned near respective opposite poles of $C_p$;

m=1-5 and Z is a hydrophilic, lipophilic, or amphiphilic chemical moiety;

n=1-5 and Y is a lipophilic chemical moiety;

p=60-120 and p is an even number; and

X, if present, represents one or more metal atoms within the fullerene (F), optionally in the form of a trinitride of formula $G_{i=1-3}H_{k=3-i}N$ in which G and H are metal atoms.

In another embodiments p=60 or 70. The prolate ellipsoid shape of $C_{70}$ provides particularly desirable advantages in synthesis and activity. In certain embodiments, each chemical moiety Z is composed of formula ArB in which A is a hydrophilic, lipophilic, or amphiphilic chemical moiety, r=1-4, and B is a chemical linker connecting said A to the fullerene, and each chemical moiety Y is composed of formula $DE_v$ in which E is a lipophilic chemical moiety, v=1-4, and D is a chemical linker connecting the lipophilic chemical moiety to the fullerene.

The synthetic fullerene molecule can be designed to have a geometrical configuration capable of causing the synthetic fullerene molecule to locate in or near phospholipid bilayers of a cell such that a radical scavenging zone near the equatorial band of the fullerene is situated within or in close proximity to the phospholipid bilayer. Such configurations include having a lipophilic moiety or moieties at one pole capable of anchoring the fullerene to a lipid bilayer and an opposing hydrophilic moiety or moieties that will tend to extend the fullerene into the lipid/water interface. Alternatively, a second opposing lipophilic moiety or moieties will tend to keep the fullerene buried within the lipid bilayer.

A plurality of synthetic fullerene molecules can be uniformly dispersed in phospholipids, such as in liposomes. Unlike some molecules that have been previously investigated, the amphipathic fullerene molecules described herein generally do not form vesicles by themselves, but require membrane-forming phospholipids in mole ratios greater than 1:1 (lipid:fullerene adduct) to form vesicles. Such liposomes can be useful delivery vehicles for the synthetic fullerenes and optionally additional active ingredients. The synthetic fullerene molecules can also be formulated in a topical composition in the form of an ointment, cream, lotion, moisturized patch or moisture-free patch, shampoo, gel, rinse, face lotion, milky lotion, paste, shaving cream, foundation, cologne, or pack.

The synthetic fullerene molecules are useful for, among other things, neutralizing reactive molecules, such as reactive oxygen species, that are produced at or near lipid membranes in cells and living organisms. The synthetic fullerene molecules can be used in a method of treating a disease or condition that is caused or exacerbated by reactive radicals, the method comprising administering a synthetic fullerene molecule as described herein to a subject in need thereof. The treatment can include administering a synthetic fullerene molecule uniformly dispersed in phospholipids by any means including ingestion, injection, suppositories, topically, etc. For example, administering a topical composition comprising a synthetic fullerene molecule uniformly dispersed therein to one or more areas of the body on which symptoms of a disease or condition appear. Topical compositions comprising the synthetic fullerene molecules described herein can be used in cosmetic formulations to ameliorate the effects of reactive molecules on skin or as stabilizers or preservatives of active ingredients during storage or after exposure to air during use.

The ability to neutralize reactive molecules can be used to ameliorate undesired side effects of other pharmaceutical molecules. The synthetic fullerene molecules can be formulated in a composition comprising in a pharmaceutically acceptable medium and another pharmaceutical molecule. Thus, treatments that have the effect of producing reactive molecules may be improved by including the synthetic fullerene molecules described herein. The usefulness of the synthetic fullerene molecules described herein is not limited to neutralizing reactive molecules. The synthetic fullerene molecules described herein can also exert biological effects by occupying binding sites in lipid associated proteins.

DETAILED DESCRIPTION

Figure 1:
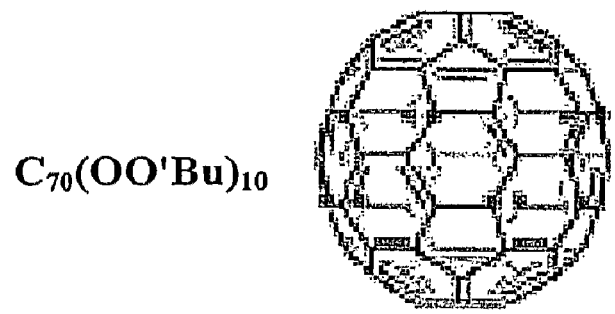
FIG. 1 illustrates that peroxide radical additions to $C_{70}$ can occur at equatorial area (dots indicate addition sites).

Aerobic organisms depend on harnessing chemical energy from the oxidation/reduction cycle to live and thus are continuously exposed to oxidative stress. Oxidative phosphorylation, the production of nucleotide tri-phosphates, e.g. ATP, is controlled through the transfer of electrons, which generates highly reactive intermediates: "free radicals."

"Free radicals" are molecules that have an unpaired electron that can make them highly reactive. The term "free radicals" is commonly used to refer to reactive oxygen species ("ROS"), but other molecules can also be free radicals. Reactive oxygen species include: free hydroxyl radicals ($OH^-$), superoxide anions ($O_2^-$), singlet oxygen ($^1O_2$), hydrogen peroxide ($H_2O_2$), organic peroxides (R—OOH), nitric oxide (NO), and peroxynitrite (ONOO—). Certain active pharmaceutical ingredients also comprise reactive groups or are metabolized to comprise reactive groups.

Free radicals are potentially damaging, even lethal, if permitted to uncontrollably oxidize macromolecules such as lipids, DNA and proteins. Tissues, cells and organelles where oxidation is prevalent normally maintain significant amounts of anti-oxidant molecules to mitigate oxidative damage. Failure of this system and uncontrolled oxidation is associated with many diseases.

Reactive species can cross link and damage many macromolecules. Reaction products whose presence is indicative of ROS activity, include 8-hydroxy guanosine (an oxidized component of DNA), O-tyrosine or dityrosine (components indicative of protein oxidation), and malondialdehyde (an indicator of peroxidation damage to phospholipids). These reactive biological macromolecules can attack whole families of related macromolecules and thereby affect a number of biological reactions. The consequences can include induction of cell death, mutation of DNA to cause cancer, inflammation and tissue degeneration. Several disease pathologies are caused by metabolic deregulated processes, flooding mitochondria, cells and tissues with highly reactive chemical species such as ROS.

Oxidative damage is used by the immune system in fighting foreign pathogens. Neutrophils and other white blood cells contain specialized lipid vesicles, called peroxisomes, filled with activated oxygen species whose purpose is to damage and/or kill invading organisms. When triggered, white blood cells self-destruct, spilling a local abundance of free radicals to overwhelm pathogens. Under normal control, these are effective tools for protection, but overaggressive deployment can overwhelm the modulating systems and provoke serious damage that can even be fatal to the host.

The immune system is one example of how loss of control of oxidative processes can have life threatening consequences but there are many others. Accumulated oxidative damage caused by smoking, chemical vapors or radiation therapy can induce destruction of the cells that produce elastic tissue in the lungs, replacing them with inelastic fibroblasts in a debilitating condition known as pulmonary fibrosis.

Degenerative diseases of neural tissue can be initiated by oxidative damage. Beal et al., "Neurodegenerative Diseases" (Cambridge University Press 2005). The brain must process large amounts of oxygen; 20% of the oxygen we breathe is consumed in the brain. Because of the level of energy produced by oxidation, there is a serious hazard for spontaneous oxidative damage. Amyotrophic lateral sclerosis (ALS) is a fatal disease in which motor neurons of the cortex, brain stem and spinal cord degenerate. The cause of ALS is unknown, but about 10% of cases are inherited. Familial ALS has been traced to a genetic defect in superoxide dismutase genes (SOD1), implicating the central role of the free radical superoxide anion in this devastating neurodegenerative disease.

Parkinson's disease results from depletion of neurons in the substantia nigra of the brain that produce the neurotransmitter dopamine. Animals treated with MPTP (methyl phenyl tetrahydropyridine) develop a disease that closely resembles Parkinsonism. Close study of this phenomenon shows that MPTP is metabolized to a compound that concentrates in mitochondria of neurons in the substantia nigra where it interferes with oxidative phosphorylation and provokes excessive free radical release and an increase in superoxides which results in apoptosis of the neurons. Beal, M. F., *Ann. N.Y. Acad. Sci.*, 991:120-31, 2003.

Alzheimer's disease is characterized by progressive cognitive and memory loss associated with deposits of inert plaque and neurofibrils which replace dead cells in the hippocampus, amygdala, and cerebral cortex. Amyloid-β peptide, which is thought to be the agent responsible for neurotoxicity has been shown recently to associate with heme groups to form peroxidases in mitochondria. Atamna, H. & Boyle, K., *Proc. Nat. Acad. Sci.*, 103:3381-86, 2006. There are many converging lines of evidence to suggest that mitochondria in nerve cells, where the bulk of the oxidative activity takes place, are a target for new therapies in several neurodegenerative diseases.

Diabetes mellitus is caused by dysfunction of the regulatory system that manages blood sugar levels. When the pancreas is functioning normally the level of insulin in the blood is titrated with great precision. Some people lose the ability to produce insulin due to the death of the specialized cells in the pancreas that synthesize the hormone in a disease known as Type 1 diabetes, which used to be called juvenile onset diabetes. The most common form of diabetes, Type 2, results from insensitivity to insulin, either because the cells lose their insulin receptors or their receptors fail to function properly.

Hyperglycemia can cause repeated oxidative stresses, especially on endothelial cells, particularly those in capillaries of the retina, mesangial cells in the kidney and neurons. Oxidative damage accumulated over time can cause a number of pathologies, including damage to the retina that often leads to blindness, heart disease, damage to peripheral nerves, kidney failure and loss of circulation in the extremities. Of particular concern is the deterioration of endothelial cells that causes weakening of the blood vessels and cardiovascular disease. Most, if not all of these side effects can be attributed to oxidative damage to the cells. When blood glucose levels are high many cell types load themselves up with sugar, which is fuel for their oxidation/reduction furnaces. If the internal concentration is excessive it stresses the control system and causes damage occasionally. The accumulated effect over many decades of insults leads to the deterioration of subject tissues.

Fullerene molecules comprise closed cages of 60 to 200 carbon atoms and may also include chemical moieties attached to the exterior or incorporated within the cage. In a general notation, $C_p$ represents a fullerene cage having p carbon atoms, $X@C_p$ represents such a fullerene cage having a chemical group X within the cage.

Fullerenes have the capacity to neutralize free radicals, such as reactive oxygen species (ROS), including those that are produced during normal metabolic processes, but that can cause extensive damage if not controlled. Fullerenes, preferably endohedral metallofullerenes containing one or more caged metal atoms, can also be used as contrast agents in biological imaging applications or as radiotherapeutics. However, the use of fullerenes for treatment of oxidative damage mediated pathologies has not been widely adopted, because of difficulties arising from inherent properties of fullerenes.

Previously, $C_{60}$ fullerenes were suggested as fullerene antioxidant therapeutics. See, e.g., U.S. Pat. No. 6,265,443. The $C_{60}$ molecule was recognized early on as a "free radical sponge." Krusic et al., *Science*, 254, 1183-85, 1991. Halogen radical additions to $C_{60}$ initiate at one of the 6,6 double bonds, and subsequent additions encircle the cyclopentadiene ring whose double bonds have been made susceptible by the initial addition. Rogers & Fowler, *Chem Comm.*, p 2357-58, 1999.

$C_{70}$ shares two hemispheres that appear very similar to two $C_{60}$ halves, but in contrast to $C_{60}$, the $C_{70}$ fullerene cage has 10 extra carbon atoms distributed around the equator, making $C_{70}$ slightly ellipsoid. The prolate ellipsoid shape of $C_{70}$ defines two poles on the long axis and an equatorial zone comprising the 10 extra carbons. The equatorial zone of 6,6 double bonds in $C_{70}$ has been calculated to be favored for ten halogen radical additions. For example, $C_{70}Br_{10}$ was synthesized by pushing the radical addition conditions to the extreme and the structure was confirmed. However, in a careful study in which subsequent additions of peroxide intermediates were isolated and characterized, Gan et al. reported that the pathway for peroxide radical additions is not limited to the equatorial zone. Xiao et al., *J. Organ. Chem.*, 70:2060-66, 2005. In $C_{70}$, peroxide radical additions can occur on 6,6 bonds near cyclopentadiene rings as well as the equatorial band of six member rings.

Figure 2:
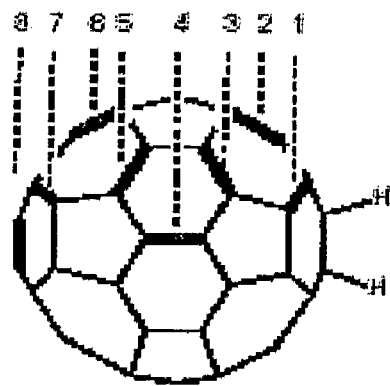
FIG. 2 illustrates eight possible adduct locations of $C_{60}$ bis-adducts
Figure 3:
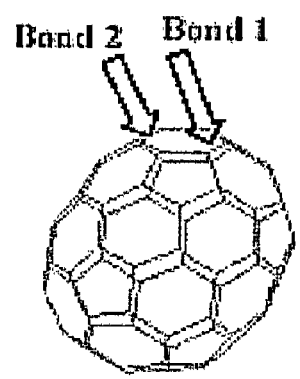
FIG. 3 illustrates two preferentially reactive bonds of $C_{70}$.
Figure 4:
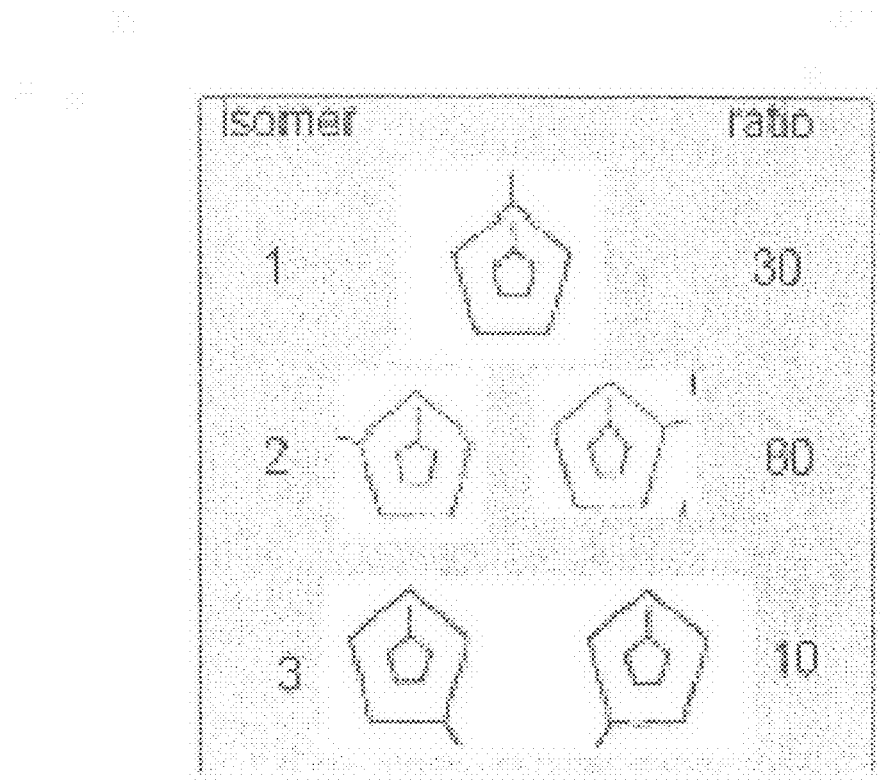
FIG. 4 illustrates a view along the long axis of $C_{70}$. Preferential addition at the $C_{70}$ poles generates three possible isomeric bis-adducts. The relative amounts of the three isomers are given in the column "ratio." The large and small pentagons represent two 5-membered rings, each at an opposing pole.
Figure 5:
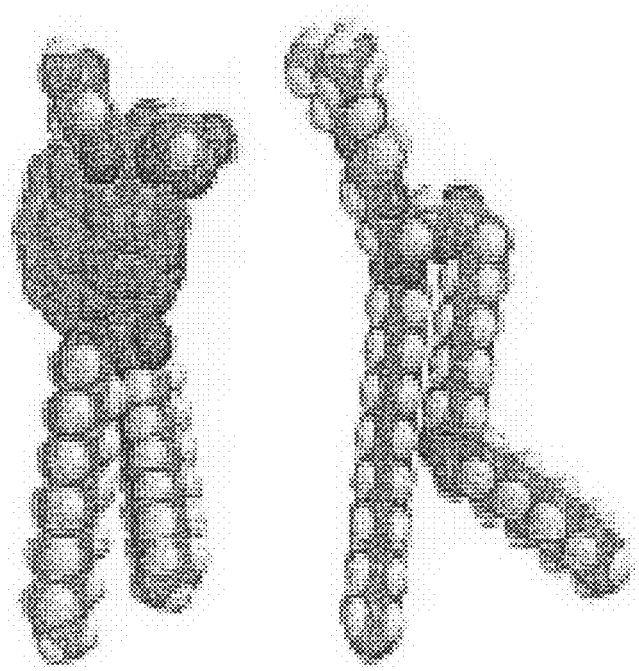
FIG. 5 illustrates a comparison of space filling models of phosphatidyl choline, on the right, with that of the amphiphilic $C_{70}$ compound 5, which is illustrated in FIG. 6.
Figure 6:
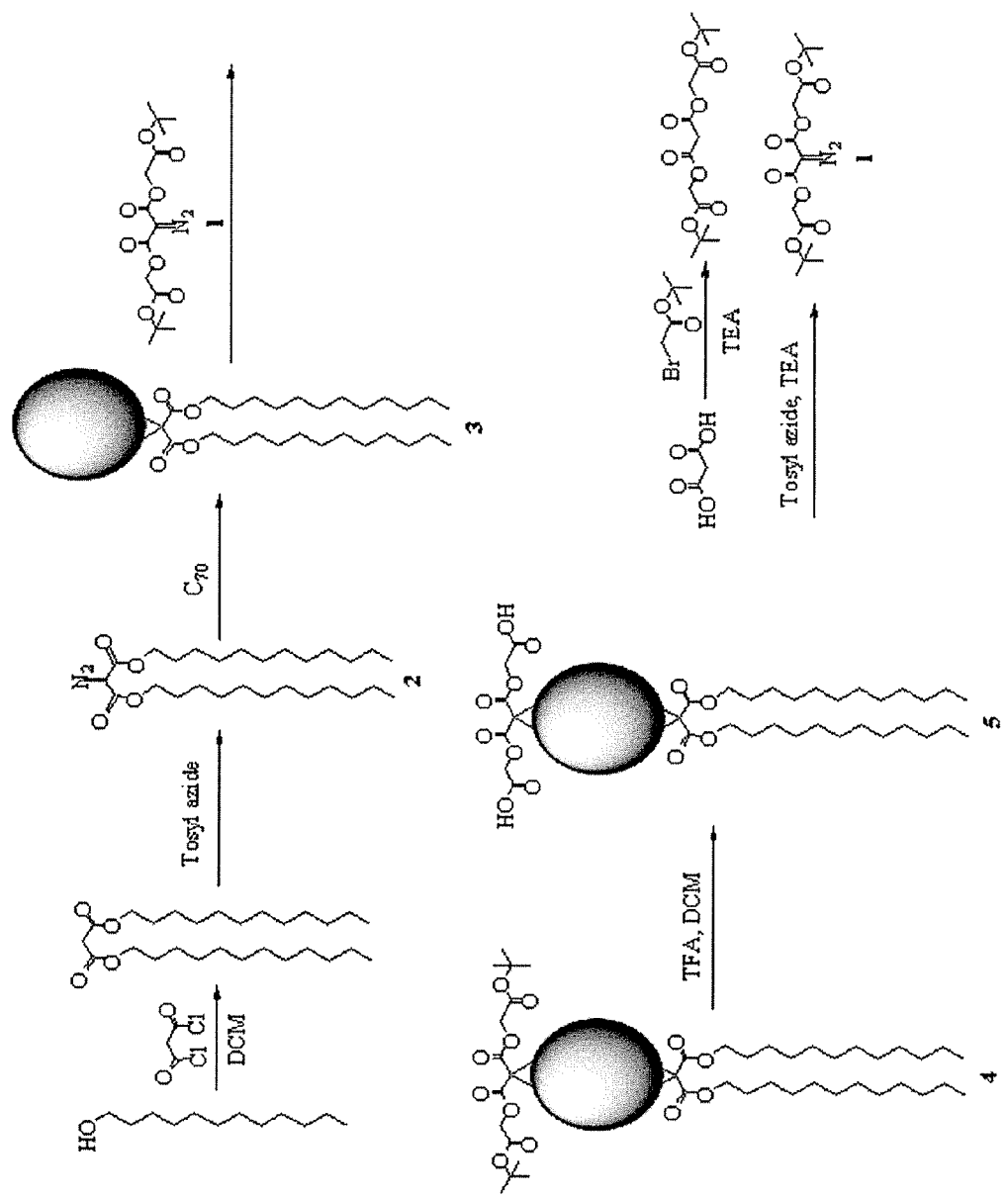
FIG. 6 illustrates a synthetic scheme for a methano amphiphilic-$C_{70}$ compound (two acid groups and two lipophilic dodecyl tails).

As illustrated in FIG. 3, nucleophilic or cyclic additions to $C_{70}$ take place at the two poles preferentially. At each pole, $C_{70}$ has a cyclopentadiene ring which reacts readily to give a mono-adduct that may appear on two bonds. Monoaddition reactions can sometimes appear on two bonds (bond 1 or bond 2) shown in FIG. 3. Nucleophilic bis-addition of malonates to $C_{70}$ takes place on bond 1 at the two poles preferentially and sequentially. Bis addition can result in the formation of three isomers, a much less complex situation than with $C_{60}$. The isomers are easily separated and distinguished by their characteristic optical spectra, as can be seen in FIG. 4. This can produce isomers in the case of multiple additions, but much less complexity than with $C_{60}$, illustrated in FIG. 2.

We have made the discovery that fullerene molecules, such as $C_{70}$, can be functionalized with targeting groups added at the molecular poles, and such addition enhances the efficacy of free radical mitigation. This is in contrast to previous reports in which the addition of adducts decreases the radical scavenging ability. See, e.g., Bensasson, supra.

Figure 9:
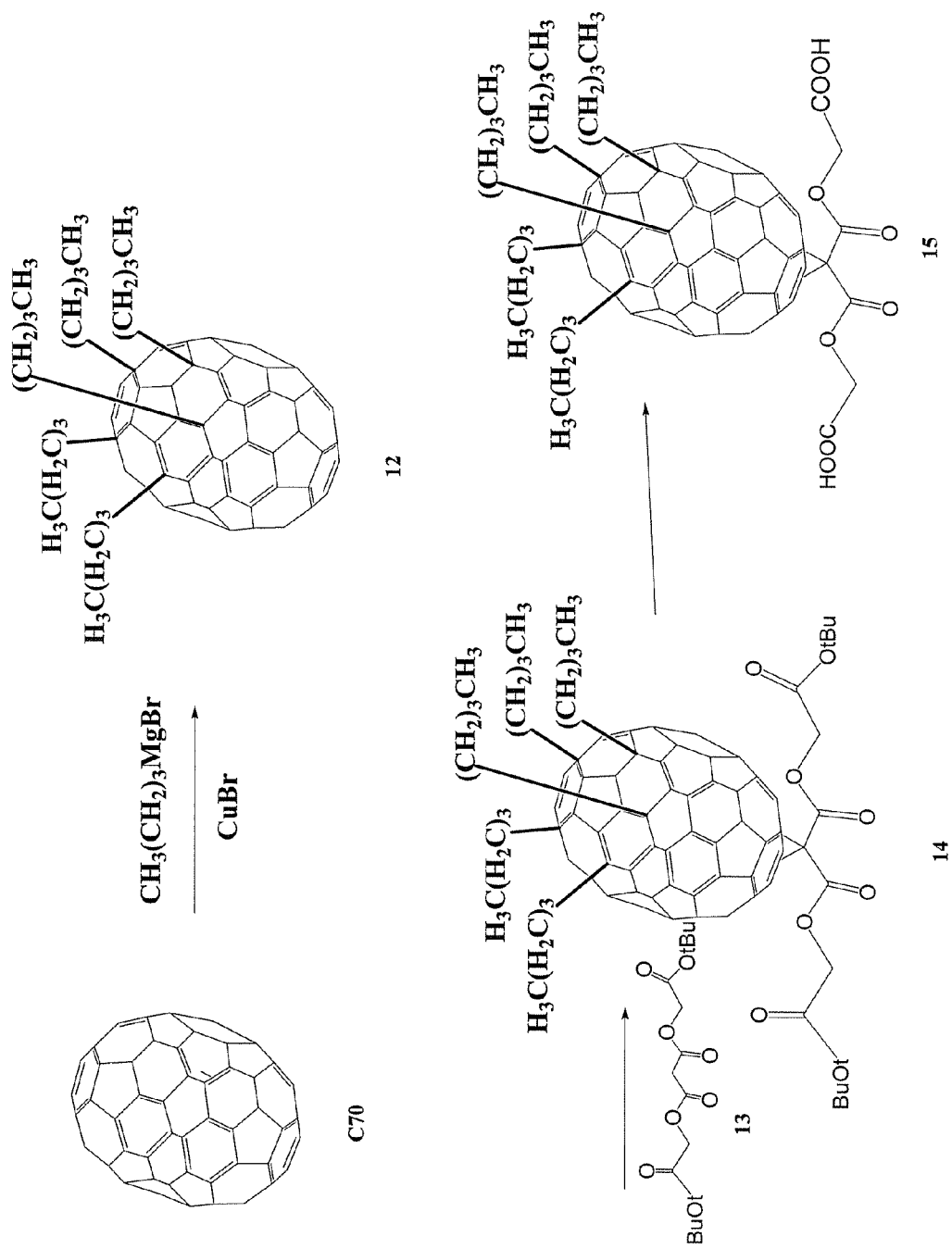
FIGS. 9-10 illustrate schemes for fivefold addition near a fullerene pole.

In certain embodiments, the synthetically modified fullerenes have functional chemical moieties covalently bound only at opposing poles of the fullerene. Where the fullerene is shaped as a prolate ellipsoid, such as $C_{70}$, the poles of the fullerene are defined by the ring of carbon atoms surrounding the long axis at each end of the fullerene. While the ellipsoid $C_{70}$ provides advantageous chemical properties for polar addition, spheroid fullerenes such as $C_{60}$ can also be preferentially functionalized at opposing poles. Where the fullerene is symmetrical, such as $C_{60}$, one pole may be defined by the location of a first functional group, with the opposing pole defined by drawing an axis through the center of a ring to which the first group is attached and through the center of the fullerene cage to a ring structure on the opposite side. It is also possible to synthetically make multiple additions near a pole. Functional groups attached at a pole are attached to one or more of the carbon atoms that form a ring immediately encircling an axis that connects two opposing poles, e.g. attached to the five member rings that encircle the long axis of $C_{70}$. Functional groups attached near a pole can be attached to the carbon atoms immediately encircling an axis through the poles or attached to carbon atoms that are bonded directly to the carbons of polar ring as illustrated in FIG. 9.

Selective addition of adducts at the molecular poles of fullerenes, can produce a molecule where subsequent radical addition reactions are predominantly limited to the equatorial region of the molecule. In various exemplary embodiments, the adduct attached at each pole can be lipophilic, hydrophilic, or a combination of lipophilic and hydrophilic groups to locate and orient the equatorial band of the fullerene in proximity to a biological membrane or synthetic lipid bilayer. By selecting functional adducts including one or two lipophilic moieties, the resulting molecule juxtaposes the radical absorbing equatorial zone of the modified fullerene with nano-scale precision to sites in or near lipid membranes where pathogenic free radicals are generated, thereby creating surprisingly potent antioxidant therapeutics. Cell membranes are comprised of bimolecular layers ("bilayers"), in which amphipathic lipids are oriented in opposing leaflets, such that the hydrophobic groups are sandwiched between two planes of hydrophilic groups. Membrane-targeted, polar modified, fullerene derivatives, preferably polar bis-adducts of $C_{70}$, as described herein are more potent free radical sponges than prior $C_{60}$ compounds. Furthermore, polar adduct fullerenes such as $C_{70}$ bis-adducts have in vitro and in vivo properties that overcome several problems presented by previously proposed fullerene derivatives in which functional groups are not restricted to the poles and may not include a lipophilic functionalized pole.

Thus, preferred modified fullerene molecules include fullerenes wherein the fullerene is preferably ellipsoid, for example, prolate ellipsoid, in shape with an equatorial band and two opposing poles, and comprises an adduct at one or both poles, at least one adduct being a hydrophobic chemical moiety capable of anchoring the fullerene on or in a lipid membrane.

In an embodiment, the synthetically modified fullerene molecule has the formula

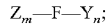

wherein F is fullerene of formula $C_p$ or $X@C_p$, the fullerene having two opposing poles and an equatorial region;
Z and Y are positioned near respective opposite poles of $C_p$;
m=1-5 and Z is a hydrophilic, lipophilic, or amphiphilic chemical moiety;
n=1-5 and Y is a lipophilic chemical moiety;
p=60-200 and p is an even number; and
X, if present, represents one or more metal atoms within the fullerene (F), optionally in the form of a trinitride of formula $G_{i=1-3}H_{k=3-i}N$ in which G and H are metal atoms.

In exemplary variations, p is an even number between 60 and 120, with p=60-96 being more common and p=60 or p=70 being preferred. The synthetically modified fullerene can be arranged wherein each chemical moiety Z is composed of formula $A_rB$ in which A is a hydrophilic, lipophilic, or amphiphilic chemical moiety, r=1-4, and B is a chemical linker connecting said A to the fullerene, and each chemical moiety Y is composed of formula $DE_v$ in which E is a lipophilic chemical moiety and, v=1-4, and D is a chemical linker connecting the lipophilic chemical moiety to the fullerene.

The fullerene can be a prolate ellipsoid shaped fullerene having a major axis such that said poles are located at opposing ends of the major axis of the prolate ellipsoid fullerene. Alternatively, the fullerene can be spheroid with opposing poles defined by an axis through opposing carbon rings. Z and Y can configured such that when the molecule is contacted with a lipid bilayer in an aqueous medium, the equatorial region of F is selectively located within or in close proximity to the phospholipid bilayer. The molecule can be configured so that in an extended configuration has an aspect ratio of about 2.1 to 15, and a diameter less than about 2 nm. Such configurations are preferred configurations for incorporation of the molecules into lipid bilayers.

In certain alternatives, a synthetic fullerene molecule has the formula $Z(C_{70})Y$; wherein Y is a lipophilic moiety covalently connected to $C_{70}$, optionally through a linking group, at or near a pole thereof, and wherein Z is a lipophilic moiety, amphiphilic moiety, or a hydrophilic moiety covalently connected to $C_{70}$, optionally through a linking group, at or near a pole opposite to said Y; and, wherein said lipophilic moiety Y is capable of anchoring the synthetic fullerene molecule to a lipid membrane.

In another embodiment, the fullerene molecule can have the formula $Z_m$—F—$Y_n$ wherein:
F is a fullerene of formula $C_p$ having p=60-200 carbons, preferably p=60, 70
m=1-5 such that each X is a group $A_rB_s$ in which r=1-4, s=1-4, and A is one or more hydrophilic or polar group bonded to the fullerene through one or more linker B;
n=1-5 and each Y is a group $D_tE_v$ in which t=1-4, v=1-4 and E is one or more lipophilic group bonded to the fullerene through one or more linker D; and,
X and Y are positioned at or near opposite poles of F.

In certain embodiments, the synthetic fullerene molecule has a geometrical configuration capable of causing the synthetic fullerene molecule to locate within phospholipid bilayers of a cell such that a radical scavenging zone near the equatorial band of the fullerene is situated within or in close proximity to the phospholipid bilayer.

A plurality of such synthetic fullerene molecules can be uniformly dispersed in phospholipids, such as in liposomes. The amphipathic fullerene molecules described herein do not generally form vesicles by themselves, but require membrane-forming phospholipids in mole ratios greater than 1:1 (lipid:fullerene adduct) to form vesicles. Alternatively, the synthetic fullerene molecules can be formulated in a topical composition in the form of an ointment, cream, lotion, moisturized patch or moisture-free patch, shampoo, gel, rinse, face lotion, milky lotion, paste, shaving cream, foundation, cologne, or pack.

The synthetic fullerene molecules are useful for, among other things, neutralizing reactive molecules, such as reactive oxygen species, that are produced at or near lipid membranes in cells and living organisms. The synthetic fullerene molecules can be used in a method of treating a disease or condition that is caused or exacerbated by reactive radicals, the method comprising administering a synthetic fullerene molecule as described in claim 1 to a subject in need thereof. The treatment can include administering a synthetic fullerene molecule uniformly dispersed in phospholipids by any means including ingestion, injection, suppositories, topically, etc. For example, administering a topical compositions comprising a synthetic fullerene molecule uniformly dispersed therein to one or more areas of the body on which symptoms of a disease or condition appear.

The ability to neutralize reactive molecules can be used to ameliorate undesired side effects of other pharmaceutical molecules. The synthetic fullerene molecules can be formulated in a composition comprising in a pharmaceutically acceptable medium and another pharmaceutical molecule. Thus, treatments that have the effect of producing reactive molecules may be improved by including the synthetic fullerene molecules described herein.

The ability to precisely position the radical reactive zone relative to its cellular environment can provide high efficacy and low toxicity not found in the previously proposed fullerene compounds. In previous fullerene compounds, reactivity has not been limited to a specific region on the fullerene and the compounds could not be precisely positioned relative to location where reactive radicals are produced or cause damage. The fullerenes described here can be made to locate preferentially at a specific cellular target location where they can be most effective. In addition, $C_{70}$ addition reactions can be performed so as to produce fewer isomers and higher yields of desired adducts, such as mono and bis-adducts, than $C_{60}$. Spheroid fullerene molecules such as $C_{60}$ can be reacted to preferentially form polar adducted fullerenes, where the poles are defined as opposing carbon rings to which the adducts have been bonded.

Formation of bis-adducts on opposite poles of a fullerene creates an anti-oxidant molecule that can be targeted with great precision to juxtapose the radical-absorbing zone at the equator of the fullerene using a combination of linkers and targeting functional groups to direct this radical-absorbing zone to highly specific targets with great precision. Free radical absorption is dependent on proximity to sites of radical addition. Therefore, the ability to precisely target the radical-absorbing zone is desirable for therapeutic applications. The shape and chemical properties of $C_{70}$ are particularly suited to provide optimal location. Polar addition of adducts on other fullerenes prolate ellipsoid and spheroid fullerenes would also confer similar benefits.

Radical addition of an unstable nitrogen:peroxide radical to $C_{70}$ has been found to be considerably more efficient than the same reaction with $C_{60}$. An unstable nitrogen radical was made by adding butanone peroxide to nitrogen immobilized on a solid substrate in the presence of either $C_{70}$, $C_{60}$ or, as a control, the anti-oxidant Vitamin E in xylene. Radical addition of the substrate to the immobilized, activated amine is measured by HPLC. Under these conditions the natural anti-oxidant did not react at all. Surprisingly, $C_{70}$ reacted far more strongly. 74% of the $C_{70}$ was bound to the nitrogen while only 27% of the $C_{60}$ was bound. This greater reactivity of $C_{70}$ observed is surprising because the differences in electron affinity are not profound ($C_{60}$=2.65, $C_{70}$=2.73).

Radical chemistry is critically dependent on the local environment in which the reactants meet. Aqueous systems are especially complex because of the mutability of water, which can contain dissolved gasses (like $O_2$), can dissociate into OH− and H+, and is affected by other solutes, pH, salts, etc. Bensasson et al. have suggested that to characterize the relative reactivity of a series of water soluble $C_{60}$ fullerene derivatives it is necessary to go to extreme lengths to control mitigating variables. Bensasson et al., "Reactions of e-aq, $CO_2^-$, HO·, $O_2^-$ and $O_2(1\ \Delta g)$ with a dendro[60]fullerene and $C_{60}$ $[C(COOH)_2]_n$ (n=2-6)" *Free Radic. Biol. & Med.,* 29:26-33, 2000. Bensasson et al. measured the kinetics of ten different water-soluble fullerene compounds for absorption and dissociation of a number of radical groups using pulse radiolysis and flash photolysis. To measure these highly specific constants they had to use extreme care over pH, had to eliminate any trace of dissolved oxygen and include solutes such as formate to obtain measurements that were not confounded by other variables. The results are remarkable for the lack of discrimination between these different species with respect to these constants. With respect to reaction with superoxide radical anion these authors teach "thus the electron transfer from $O_2^-$ to F becomes increasingly difficult with increasing attenuation of the conjugated fullerene π chromophore." The more modifications made to $C_{60}$ to increase its water compatibility the less effective it is in binding superoxide radicals. By contrast, the polar adducts described herein provide for a targeted equatorial absorption zone with minimal occupation of sites on the fullerene.

Biological systems are orders of magnitude more complicated than simple aqueous solutions. For example, compartments of particular interest in which pathogenic free radicals are generated include mitochondria. These organelles are highly complex, with several internal aqueous compartments bounded by phospholipid membranes. Within both the membrane and aqueous compartments are thousands of proteins, some of which are partially integrated in membranes, some of which are not. In addition there are literally streams of oxygen molecules supplying the respiratory chain that generates ATP, constantly fluctuating pools of anti-oxidants, electron carriers, cations, anions, sugars, amino acids, nucleotides in a continuously changing environment. Mitochondria are one example, but there are many other micro-environments within cells that are likewise dynamic and contribute to pathologic conditions.

To achieve successful control over the generation of pathogenic radicals it is desirable to assume control of the local, nano-scale, environment where the free radicals are being generated. The ability to position a molecular zone to which high energy radicals will react precisely at the intracellular target is a desirable capability in managing radical mediated pathogenesis.

Addition chemistry for making derivatives of fullerenes has recently been reviewed. Hirsch and Brettreich "Fullerenes: Chemistry and Reactions" (Wiley-VCH, 2005). Addition of functional groups on fullerenes occurs by attacking one of the shared electrons in the aromatic rings to ligate another atom or molecule to the sphere. Spherical fullerenes such as $C_{60}$ have multiple bonds which are indistinguishable, so addition of more than one group to the sphere produces multiple isomers-molecules with the same structural formula but different shapes.

Multiple isomers can be problematic for pharmaceutical applications. Molecules which are isomers of each other may, and often do, have completely different biological properties. Such variability in behavior has been known to have fatal consequences, and thus is of high importance from a safety perspective. For example, eight isomers can be formed when two addition groups are attached to a $C_{60}$ sphere. These different isomers can often be separated by high performance liquid chromatography due to the rigid 3D display of functional groups on the fullerene core molecule, leading to distinctive chromatograhic properties. Likewise, addition of three groups to $C_{60}$ produces 43 possible isomers.

The addition of targeting groups to the poles of a $C_{70}$ molecule leaves the equatorial radical zone exposed for radical additions. Thus the structural selectivity and stereochemistry of polar functionalized $C_{70}$ is well suited for therapeutic applications, because it enables precise control of a specific reactive zone situated between targeting moieties on opposing poles. Attaching targeting moieties to each pole with linkers customized for specific sites enables very precise engineering of the fullerene derivative to juxtapose the radical absorbing zone with its target. Radicals, especially pathogenic radicals, are highly reactive and a radical absorbing agent will be most effective when positioned in the immediate presence of the radical to quench the reaction and neutralize the radical before it propagates to damage macromolecules such as DNA, lipids and proteins.

The geometry of asymmetric amphipathic fullerene bisadducts, such as $C_{70}$ in which a lipophilic moiety is attached at one apical cyclopentadiene ring and a polar or charged group is attached to the opposite apical cyclopentadiene ring, results in amphipathic compounds that may intercalate into membrane bilayers readily if their shape and size is similar to that of phospholipids. Ability to intercalate into lipid bilayers can be predicted from the molecular aspect ratio. If the length of the molecule is $\geq 2.1$ times the diameter of the fullerene, the compound is amenable to stable intercalation into bilayers. Length refers to an extended model conformation. If the length greatly exceeds the bilayer width, the compound would tend to destabilize bilayers, as is well known from studies of proteins in membranes e.g. Heimburg (Thermal Biophysics of Membranes, Wiley, 2007). Thus, a preferable upper limit of the aspect ratio is about 15. Previously suggested functional groups that are extensively branched, such as dendrimers, are also likely to destabilize the cell bilayer. Likewise, multiple lipophilic additions, such as described in Hirsch et al., *Angew. Chem. Int. Ed.*, 39:1845-1848, 1999, are likely to destabilize cell bilayers.

In another embodiment, it may be desirable to synthesize fullerene derivatives to which lipophilic moieties are attached at both poles. Such compounds would accumulate in and potentially mitigate free radicals in triglyceride deposits. Such lipophilic fullerene antioxidants could be used for topical application, either for dermatological applications or other topical applications, e.g., otic, ophthalmic, vaginal, rectal, buccal use. Such lipophilic fullerene compounds may contain saturated or unsaturated fatty acids, including biologically active lipids such as eicosanoic acid, cardiolipin or phosphatidyl esters.

Targeting of polar adduct fullerene molecules to specific cellular locations and even to specific depths in association with lipid membranes can be accomplished by the choice of adducts and linker moieties. For example, lipophilic bis-adducts comprising two mono- or di-acyl moieties can cause the derivatized fullerene to locate preferentially in the centers of lipid bilayers. Bis-adducts comprising one lipophilic moiety and one hydrophilic moiety can position the radical absorbing equatorial region of $C_{70}$ or another fullerene in the lipid interface with the lipophilic moiety intercalated into the membrane and the hydrophilic moiety directed towards the water phase at the lipid interface. By selecting linking groups of appropriate polarity and dimension, the depth that the radical absorbing equatorial band of the $C_{70}$ can be moved more or less toward the center of a lipid bilayer.

Figure 7:
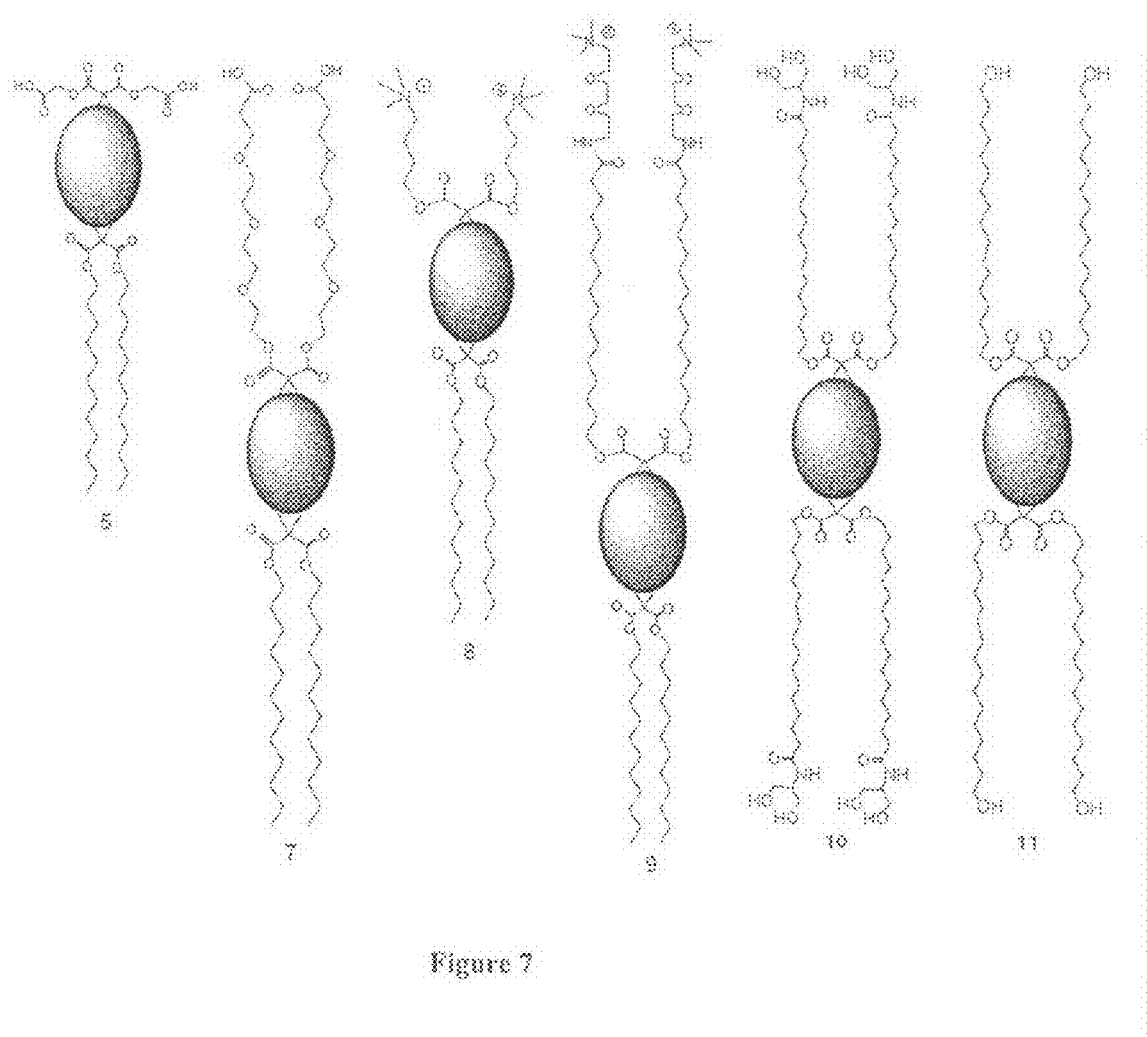
FIG. 7 illustrates examples of amphiphilic $C_{70}$ compounds with varying distance between the polar heads and $C_{70}$.
Figure 8:
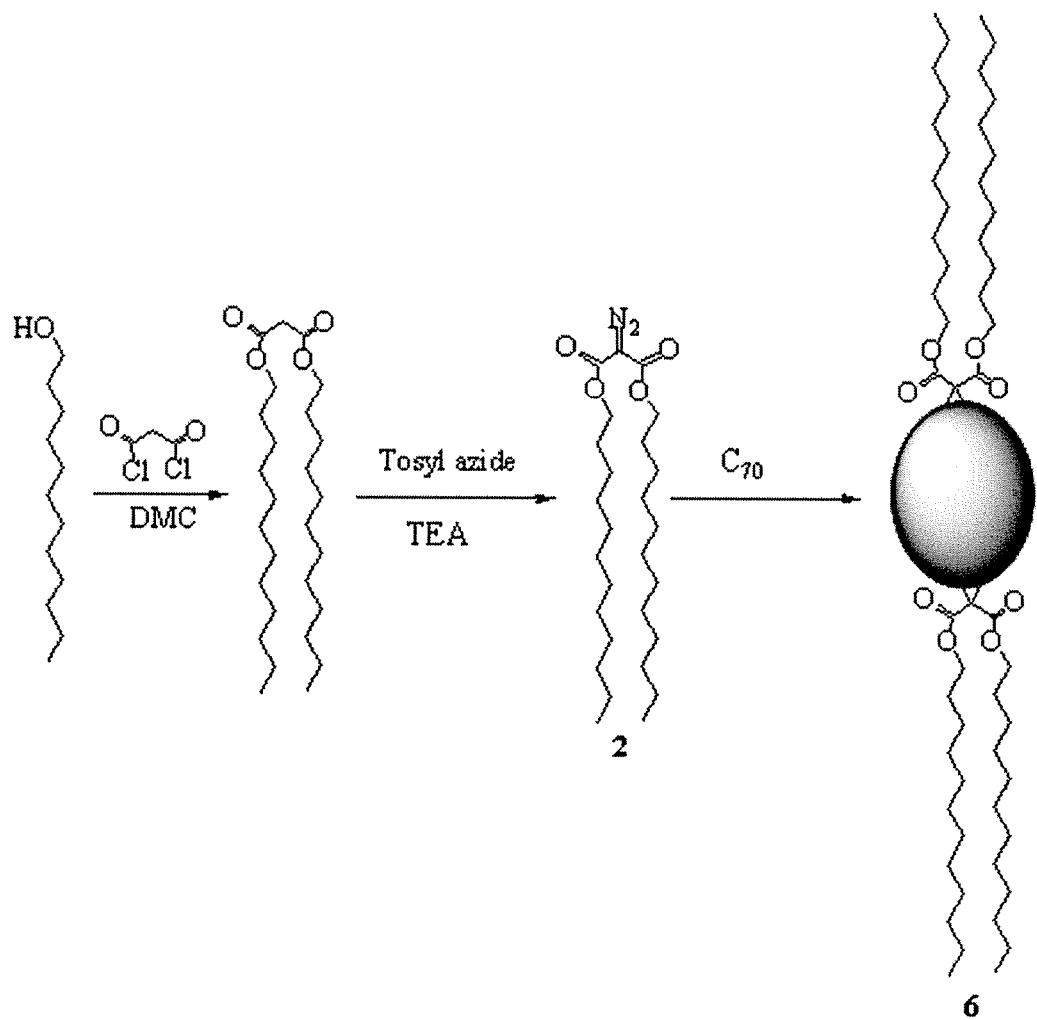
FIG. 8 illustrates the synthesis of a $C_{70}$ bisadduct.

Adjusting the linker between the polar groups and the fullerene core can position the fullerene in a selected site inside the lipid bilayer membrane. Linkers can comprise 1, 2, 3, 4, 5, 6, 7, or more atoms in a chain between the functional moiety and the fullerene. Linkers can comprise C, N, S and O atoms and can be lipophilic, amphiphilic or hydrophilic. In this way, the radical absorbing zone can be precisely positioned in proximity of where radicals are generated, so that radicals will be scavenged immediately after generation, limiting damage to a minimum. FIG. 7 shows a few examples of $C_{70}$ compounds with various arrangements. Generally, the lipophilic groups will be anchored among the acyl chains of a lipid bilayer, while polar groups are positioned in the interface or the water layer proximate to the interface. In the polar groups, the acid polar groups can be substituted by quaternary amine cations.

Biological lipid membranes are far from being homogenous. Different membranes of various organelles have distinct compositions from each other and from the cellular membrane. Moreover, the inner and outer leaflets of membranes can have distinct compositions of predominant acyl chain types and hydrophilic groups among lipids. Thus, polar modified fullerenes, such as $C_{70}$ bis-adducts, may be targeted preferentially to a desired cellular compartment by choice of an appropriate compatible adduct. For example, cardiolipin is a lipid found in inner mitochondrial membranes. $C_{70}$ with a polar adduct of cardiolipin will accumulate in inner mitochondrial membranes. Likewise inner membranes have relatively little cholesterol, while outer membranes are relatively rich in cholesterol. $C_{70}$ with a cholesterol attached to one pole will be enriched in outer mitochondrial membranes.

Adducts can be attached at the poles of ellipsoid fullerenes such as $C_{70}$ by any suitable chemical reaction. Preferred reactions and conditions resulting in mono-adducts include nucleophilic additions such as cyclopropanation, organolithium addition, Grignard addition and acetylene addition, and cycloadditions such as [3+2]cycloadditions, diazo addition, Diels-Alder cycloaddition and benzyne addition. Preferred reactions and conditions include those described in Fullerenes—Chemistry, Physics and Technology (Wiley, 2000) Kadish and Ruoff, editors, and "Fullerenes: Chemistry and Reactions" (Wiley-VCH, 2005) by Hirsch and Brettreich.

Lipophilic moieties are chemical moieties that in isolation would partition into oil, e.g., olive oil, substantially more than water. Lipophilic moieties are substantially non-polar. Suitable lipophilic moieties include saturated and unsaturated fatty acids and acyl alcohols. Preferred lipophilic moieties include fatty acids, steroids and diacylglycerol. Generally the acyl chains can be saturated or unsaturated and comprise 10, 11, 12, 13, 14, 15, 16, 17, 18 or more carbons. The synthetically modified fullerenes described herein preferably have at least one lipophilic moiety connected by a linker to a carbon on at least one pole of a fullerene. Generally, the lipophilic moiety has the function of anchoring the fullerene to a desired location in, or proximate to, a lipid membrane.

Hydrophilic moieties are chemical moieties that in isolation would partition into water substantially more than oil, e.g., olive oil. Hydrophilic moieties are generally polar and may include atoms carrying an electronic charge. Suitable hydrophilic moieties include choline, ethanolamine, serine, phosphates, acids, and amides. Preferred hydrophilic moieties include malonate, nucleotides, peptides, cofactors, e.g., glutathione or flavone and sugars. Other hydrophilic adducts are also contemplated. Amphipathic fullerenes with cofactors may cause them to accumulate with greater precision to other intracellular compartments. For example, it may be desirable to target amphipathic fullerenes to the cell nucleus by addition of nucleotides to the polar end of the fullerene. Short peptides that route traffic within cells may be used to direct the amphipathic fullerene to other intracellular compartments such as endoplasmic or sarcoplasmic reticulum or the Golgi apparatus. The hydrophilic moiety can be used to direct the fullerene reactive zone near specific sites within bilayers. Likewise the lipid addition group may facilitate compartmentalization as well. It is known that cardiolipin is abundant in inner mitochondrial membranes for example. Certain fatty acids, in particular polyunsaturated fatty acids are signal molecules in some inflammatory cascade reactions when mobilized by phospholipase C. For example eicosanoic acids play a critical role in various inflammatory responses. Trafficking of such lipophilic species may facilitate delivery of the amphiphilic fullerene for specific therapeutic applications. It is possible to alter the position of the $C_{70}$ reactive zone within the bilayer by attaching different tethers between the hydrophilic moiety and the fullerene and/or between the lipid moiety and the fullerene. The reactive zone is approximately 0.5 nm wide, while the bilayer width is more than 10 nm. It may be desirable to position the reactive zone at very specific depths within the bilayer to optimize activity in specific settings.

Amphiphilic moieties are chemical groups comprising both hydrophilic and hydrophobic features. The synthetically modified fullerenes described herein can have one or more hydrophilic or amphiphilic moiety connected by a linker to a carbon at on the opposite pole of the fullerene from a lipophilic moiety. Generally, the hydrophilic or amphiphilic moiety has the function of positioning the equatorial band of the fullerene relative to the water/lipid interface of a lipid membrane.

Linking groups can be lipophilic or hydrophilic or amphiphilic and of a length that is in accordance with the desired location of the equatorial band. For example, preferred linking groups include poly methoxy groups, e.g., glyme, aromatic species or alkanes. In general the linker may comprise alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl groups. In particular embodiments, the connecting group can form a cyclopropyl ring comprising one linker carbon and two fullerene carbons. The linker is generally a small chemical group, typically comprising less than about 8 carbon atoms, the precise size selected according to the desired position of the fullerene. Accordingly, the linker can comprise 1, 2, 3, 4, 5, 6, 7, 8 or more atoms separating a functional group from a fullerene.

A problem that has impeded the use of fullerenes as neutralizers of ROS and other free radicals in vivo has been the difficulty of stable, safe and effective carrier compositions. Fullerenes are insoluble in many common organic solvents and are not soluble in aqueous solution. Thus, it would not be desirable to inject unmodified fullerenes directly into living organisms. Chemical modifications to the fullerene that add charged and/or polar groups can increase aqueous solubility. However, even with chemical modification, these fullerenes may aggregate into complexes large enough to block capillaries. Addition of multiple polar groups to each fullerene may solve the aqueous solubility problem, but can introduce new complexities. For example, because there are multiple sites on the fullerene to which reactive polar groups can bind, the reaction products are typically mixed isomers, which may be undesirable for pharmaceutical formulations.

It has now been discovered that spheres formed of phospholipid molecules, for example, spheres made up of one or more lamella of phospholipid molecules organized into bilayer structures can be made comprising a substantially uniform distribution of lipophilic or amphiphilic fullerene molecules comprising a mono- or bis-adduct of lipophilic moieties or a bis-adduct comprising a lipophilic moiety and a hydrophilic moiety.

Such compositions possess characteristics that make them suitable for use as pharmaceuticals, and can be reproducibly and stably manufactured. Useful fullerenes are preferably $C_{70}$ fullerene adducts, but also fullerene molecules having between about 60 to 200 carbon atoms in the fullerene sphere, and which have surfaces that differ in chemical reactivity for addition of adducts. Adducts may be desirable to achieve disposition at the target where the fullerene pharmaceutical activity is most effective. Adducts may also be desirable to optimize the fullerene activity, such as by tuning the electron affinity of the fullerene such that it reacts with undesirable free radicals yet does not interfere with vital electron transfer. Other fullerenes that may be used include endohedral metallofullerenes with the formula $X_i@C_m$, where X is a metallic element and i=1 or 2 and m is between about 60 and about 200. A preferred embodiment for contrast agents is a trimetallic nitride endohedral fullerene having a general formula $A_{3-n}X_nN@C_m$ where n ranges from 0 to 3, A and X may be trivalent metals and may be either rare earth metal or group IIIB metals, m is between about 60 and about 200. This class of endohedral metallofullerenes has surface zones that differ in chemical reactivity for addition of adducts at selective sites. The carbon rings directly above the enclosed metal atoms are affected by the presence of the metal, altering the susceptibility of the π orbital electrons to react. It can also be advantageous to form adducts $C_m(R_q)$, $X_i@C_m(R_q)$, or $A_{3-n}X_n@C_m(R_q)$, where $R_q$ represents one or more substituents preferably comprising organic group(s). Functional groups may provide higher and more uniform incorporation into liposomes, targeting to tissue or cellular compartments, or other functionalities.

Such compositions can be used wherever it is desirable to neutralize free radicals and ROS, for example in vivo, topically, as an ingredient in a cosmetic composition, or where delivery of metallofullerenes for therapeutic or imaging applications (e.g., in diagnostic or experimental imaging). Fullerenes can be incorporated into liposomes that contain, in addition, molecules that have biological activity, e.g., in combination therapy or combined with agents that affect the biodistribution of the liposomes to target specific tissues or cellular compartments. Liposomes incorporating fullerene molecules may also be used to encapsulate highly reactive molecules so that the reactive molecule is kept passive until the liposome reaches its target and the contents are separated from the liposome.

Phospholipids are molecules having a glycerol backbone to which two hydrophobic fatty acids and a hydrophilic polar head group are esterified. In the presence of aqueous solutions these phospholipids self-organize such that the hydrophobic fatty acid tails mix with each other and the polar head groups face the aqueous solvent. When organized in this manner into a configuration having two hydrophilic faces and a hydrophobic interior, the structure is known as a bimolecular layer, or bilayer. Various phospholipid-like molecules (such as synthetic molecules) may also be used that use non-ester linkages.

Such bilayers mimic the configuration of lipids in cell membranes. Spheres made of lipid bilayers may be called vesicles or liposomes. Liposomes (lipid vesicles) are formed when thin lipid films or lipid cakes are hydrated and stacks of liquid crystalline bilayers become fluid and swell. The hydrated lipid sheets detach during agitation and self-close to form large, multilamellar vesicles (MLV) which prevents interaction of water with the hydrocarbon core of the bilayer at the edges. Once these particles have formed, reducing the size of the particle requires energy, for example sonic energy (sonication) or mechanical energy (extrusion).

Liposomes for transport and delivery of fullerene compositions can comprise any mixture of lipids and other components conventionally used in liposomes. However, it has been surprisingly discovered that liposomes prepared principally comprising phosphatidylcholine (PC) in combination with a non-PC phospholipid such as phosphatidylethanolamine (PE) were capable of incorporating significantly higher concentrations of fullerene compounds. For example, by selecting a mixture of lipids, greater concentrations of fullerene can be incorporated without the appearance of crystals. The liposomes appear in the microscope to be substantially uniform, characterized by a yellow-green tinting of the liposomes that indicated that fullerene, was more or less uniformly distributed through most of the liposomes. It has also been discovered that the addition of an adduct or adducts that facilitates dispersion of the fullerene within the lipid bilayer, for example, cholesterol or dodecylamine can enhance the ability of fullerenes to incorporate into liposomes and improve the performance. Combinations of different tethers and adducts can be used to manipulate where in the lipid portion of the bilayer the fullerene is positioned, which may be useful in optimizing its performance as a therapeutic.

Fullerenes, such as $C_{70}$, functionalized with one or two lipophilic moieties or optionally a lipophilic moiety and a hydrophilic moiety, and preferably functionalized at the pole (s) of the fullerene, are particularly well suited to be transported and delivered in liposome compositions. These molecules can be dispersed in liposomes at higher concentrations with less tendency to aggregate or precipitate. These molecules may also be formulated in suspensions stabilized by amphiphilic molecules and in ointments, gels, creams, and the like for cosmetic and/or therapeutic application.

With regard to compositions, "principally comprising" means that the majority or plurality component of a mixture is the principal component and is intended to account for the intentional and unintentional inclusion of other minor components. "Substantially pure" means that a composition contains only the named components and such other components as may be unintentionally present as byproducts of production, due to imperfect purification, chemical reaction or degradation of named components, or other processes. No recitation of any composition in this document is meant to be interpreted as perfectly pure; rather composition purities are understood to correspond to what would be reasonably expected by practitioners in the field and tolerated for the intended use of a composition.

Accordingly, liposomes comprising fullerene molecules for pharmaceutical administration preferentially comprise a mixture of PC and non-PC phospholipids. In further preferred embodiments, liposomes include anionic phospholipids present in sufficient concentration to minimize liposome aggregation. In some compositions, the liposomes may comprise additional components that can affect the stability and physical characteristics of the lipids, for example fatty acid molecules; cholesterol, other lipids or lipid-like molecules including triglycerides, amphipathic molecules (e.g., surfactants and bile acids), and the like, or components introduced to target the liposomes to a particular site in the organism or to a cellular compartment, for example antibody or antigen fragments derivatized to lipophilic chains, glycolipids, and the like.

Lipids which can be employed in making liposome formulations comprising fullerenes include lipids having head groups of phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, preferably in combinations comprising PC as a principle component. The phospholipids can be synthetic or derived from natural sources such as egg or soy. Saturated phospholipids such as hydrogenated soy PC may also be used. In the preferred embodiments, the phospholipids are mixtures of natural extracts of PC and PE or synthetic mixtures such as dimyristoyl PC (DMPC) and dimyristoyl PE (DMPE), used in combination in any mole ratio, from 99:1 to 1:99 PC:PE. Lipids principally having myristoyl chains may be chosen because the Tc of di-myristoyl lipids falls in a preferred range below or near physiological temperatures depending on the head group and the presence of other components. Fullerene containing liposomes preferably comprise PC mixed with sufficient non-PC lipid such as PE to make a 19:1 mole ratio, or about a 9:1 or 7:3 mole ratio, up to about 2:8 or 1:9 mole ratio of PC to non-PC lipids. PG, PS, PI, SPM and PA may also be used in combination with a lipid mixture comprising principally PC and PE in amounts sufficient to confer a charge distribution to the lipid vesicles.

The liposomes can also contain a steroid component as part of the lipid phase, such steroids may be cholesterol, coprostanol, cholestanol, cholestane, steroids derived from plants, protists or fungi, such as ergosterol, steroid derivatives, such as polyethylene glycol derivatives of cholesterol (PEG-cholesterols), organic acid derivatives of sterols such as cholesterol hemisuccinate (CHS), desoxycholate, and the like. Further components of suitable mixtures can include fatty acids such as myristic acid, isopropyl myristate, isostearic acid, sucrose distearate, propylene glycol monostearate, and cetylated monoglyceride. Other substances that can be employed include lipids such as trimyristin, the fatty alcohols such as cetyl alcohol and myristyl alcohol, and fatty esters such as myristic acid ethyl ester. The addition of surfactants such as those commonly used in the drug and cosmetic composition formulations can also enhance the uptake and uniform distribution of fullerenes in liposomes.

Organic acid derivatives of tocopherols may also be used as liposome-forming ingredients, such as alpha-tocopherol hemisuccinate (THS). Both CHS- and THS-containing complexes and their tris salt forms may generally be prepared by any method known in the art for preparing liposomes containing these sterols.

Lipids from biological sources (e.g., egg, porcine, bovine, or soybean) typically contain significant levels of polyunsaturated fatty acids and therefore are inherently more susceptible to oxidation than saturated synthetic lipids. While saturated lipids offer greater stability in terms of oxidation, they also have much higher transition temperatures and thus present other difficulties in formulation. It has been found that the presence of unsaturated lipids may enhance fullerene incorporation and stability. Monounsaturated lipids are preferred, for example lipids containing oleic acid (18:1, cisΔ9) provide unsaturation, and can be much more stable than polyunsaturated compounds. Cis unsaturated bonds impart different properties to lipid acyl chains, typically increasing the local disorder in acyl chain packing, which can lower phase transition temperatures and energetically favor the accommodation of heterogeneous molecules among the acyl chains. Hydrogenated lipids have trans unsaturated bonds.

Fullerene containing liposomes or lipid complexes for use as therapeutic agents will preferably stably incorporate at least about 15% to 30% fullerene molecules by weight, but may be up to about 50% or 60% fullerene molecules by weight. Formulations may also be described by reference to the molar ratios of components. Fullerene containing liposomes or lipid complexes for use as therapeutic agents will preferably stably incorporate at least about 1:9 molar ratio of fullerene to lipid, more preferably at least about 1:6 or 1:4 to about 2:3, but may be up to about 1:1 or 2:1.

Stability issues due to hydrolytic degradation is a general problem with lipid products. However, it has been discovered that the presence of fullerene molecules in liposomes can provide a buffer against oxidation and degradation of the lipids. It has also been found that the addition of adducts to fullerenes can provide stability benefits. For example, the presence of a cholesterol group attached to a fullerene can stabilize the lipid membranes to hydrolysis by reducing the extent of water permeation into the lipid bilayers. This ability of fullerenes, or fullerene adducts to stabilize the liposomes can also be advantageous for use where the liposomes include an additional therapeutic agent which is subject to oxidative damage. These fullerene or fullerene adduct stabilized liposome formulations enable delivery of active pharmaceutical ingredients with readily oxidized or reduced functional groups.

A procedure for preparing liposomes generally comprises preparation of the lipid for hydration, hydration with agitation, and sizing to a homogeneous distribution of vesicles. When preparing liposomes with a mixed lipid composition, the lipids can be first dissolved and mixed in an organic solvent to assure a homogeneous mixture of lipids. This process is carried out using chloroform or chloroform:methanol mixtures, toluene, tertiary butanol or cyclohexane, dichloromethane, or other suitable solvents with chloroform being most common. Typically, lipid solutions are prepared at 10-20 mg lipid/ml organic solvent, although higher concentrations may be used if the lipid solubility and mixing are acceptable. A pre-selected amount of fullerene to be incorporated into the lipid bilayers of liposomes in a suitable solvent can be mixed with the lipids at this point.

Once the liposome components are thoroughly mixed in the organic solvent, the solvent can be removed to yield a lipid film. For small volumes of organic solvent (<1 mL), the solvent may be evaporated using a dry nitrogen or argon stream in a fume hood. For larger volumes, the organic solvent can be removed by rotary evaporation yielding a thin lipid film on the sides of a round bottom flask. The lipid film can be thoroughly dried to remove residual organic solvent by placing the vial or flask under vacuum for about 8-12 hours.

To remove less volatile solvents, the lipid solution can be transferred to containers and frozen, for example by swirling the container in a dry ice-acetone or alcohol (ethanol or methanol) bath. After freezing completely, the frozen lipid cake is placed under vacuum and lyophilized until dry (which may take 1-3 days depending on volume). Dry lipid films or cakes can be removed from vacuum and stored frozen and sealed until ready to hydrate.

Hydration of the dry lipid film/cake can be accomplished simply by adding an aqueous medium to the container of dry lipid and agitating. The temperature of the hydrating medium is preferably above the gel-liquid crystal transition temperature (Tc) of the lipid with the highest Tc before adding to the dry lipid. After addition of the hydrating medium, the lipid suspension is preferably maintained above the Tc during the hydration period. A hydration time of at least about 1 hour with vigorous shaking, mixing, or stirring is preferable, although the appropriate time can depend on the composition. Allowing the suspension to stand for about 8-12 hours prior to sizing the liposomes may makes the sizing process easier and improve the homogeneity of the size distribution.

Suitable hydration media include pharmaceutically acceptable aqueous buffers or distilled water and may include nonelectrolytes such as sugar solutions. Physiological osmolality (290 mOsM/kg) is recommended for in vivo applications, examples include 0.9% saline, 5% dextrose, and 10% sucrose solutions. Additional pharmaceutically acceptable solutions and components commonly used in pharmaceutical formulations are well known to the skilled practitioner. See, e.g., "Remington: The Science and Practice of Pharmacy," (Lippincott Williams & Wilkins; 21st edition, 2005).

During hydration some lipids form complexes unique to their structure. Highly charged lipids have been observed to form a viscous gel when hydrated with low ionic strength solutions. The problem can be alleviated by addition of salt or by downsizing the lipid suspension. Poorly hydrating lipids such as phosphatidylethanolamine present in molar ratios greater than 60% have a tendency to self aggregate upon hydration.

The product of hydration in this manner is a large, multilamellar vesicle (MLV) analogous in structure to an onion, with each lipid bilayer separated by a water layer. The spacing between lipid layers is dictated by composition with layers formed of lipids containing no net charge being closer together than highly charged layers which separate based on electrostatic repulsion. Once a stable, hydrated MLV suspension has been produced, the particles can be downsized by a variety of techniques, including sonication or extrusion.

Disruption of MLV suspensions using sonication typically produces small, unilamellar vesicles (SUV) with diameters in the range of 15-50 nm. Bath sonicators can be used for preparation of SUV. Sonication of an MLV dispersion can be accomplished in a bath sonicator by placing a container of the suspension in the bath sonicator for 5-10 minutes at a temperature above the gel-to liquid crystal phase transition temperature (Tc) of the lipid.

Under sonication, the MLV suspension will begin to clarify to yield a slightly hazy transparent solution. The haze is due to light scattering induced by residual large particles remaining in the suspension. These particles can be removed by centrifugation, filtration, or other means to yield a clear suspension of SUV. Mean size and distribution is influenced by composition and concentration, temperature, sonication time and power, volume, and sonicator tuning. SUV are inherently unstable and will spontaneously fuse to form larger vesicles when stored below their phase transition temperature.

Lipid extrusion is a technique in which a lipid MLV suspension is forced through a polycarbonate filter with a defined pore size to yield particles having a diameter near the pore size of the filter used. Prior to extrusion through the final pore size, MLV suspensions can be disrupted either by several freeze-thaw cycles or by prefiltering the suspension through a larger pore size (typically 0.2 µm-1.0 µm). This method helps prevent the membranes from fouling and improves the homogeneity of the size distribution of the final suspension. As with all procedures for sizing MLV dispersions, the extrusion is preferably done at a temperature above the Tc of the lipid. Attempts to extrude below the Tc will be unsuccessful as the membrane has a tendency to foul with rigid membranes which cannot pass through the pores. Extrusion through filters with 100 nm pores typically yields large unilamellar vesicles (LUV) with a mean diameter of 120-140 nm. Mean particle size also depends on lipid composition and is quite reproducible from batch to batch.

Analogous to extrusion through a filter, a mixture of MLV can be reduced to a uniform size of liposomes by passing one or more times through a small nozzle. As an example, the mixture of hydrated liposomes may be passed through a milk homogenizing system adapted to produce uniformly sized small vesicles.

Various other techniques for introducing phospholipids to water have been utilized, including ethanol injection, detergent dialysis and reverse phase evaporation. Szoka, F. & Papahadjopoulos, D., *Proc. Nat. Acad. Sci.*, 75:4194-4198, 1978. The latter method was originally developed to make large unilamellar vesicles, but was subsequently adapted for making other types of liposomes and lipid particles. Gruner, S., Lenk, R., Janoff, A. & Ostro, M. *Biochemistry*, 24:2833, 1985; U.S. Pat. No. 5,616,334.

The reverse phase method comprises providing two immiscible liquids, water and an organic solvent. The organic phase is initially present in excess, has a relatively low boiling point, is volatile and is one in which phospholipids are highly soluble. The aqueous phase contains solutes such as salts to establish osmolarity, buffer to control pH and can include water soluble drugs. The solvent mixture is dispersed by ultrasonic vibration using a bath sonicator and the organic solvent is evaporated either by vacuum or sparging with an inert gas such as $N_2$. At the solvent:water interface the phospholipids form into bilayers, although those far from the interface arrange randomly. As the volume of organic solvent reduces the mixture becomes frothy, as the surface tension of the lipids at the interface stabilizes the emulsion. When the mixture switches from a water in solvent emulsion to a solvent in water emulsion the liposomes begin forming. Ultrasonic dispersion energy maximizes the interface and thorough mixing of water solutes is the result.

A preferred method for preparing fullerene liposomes is a reverse-phase method. The reverse phase evaporation method is based on creating, first, a water in oil phase system which is then converted into an oil in water system. Surprisingly, fullerene molecules remain associated with the lipids during the transition from a water in oil system to an oil in water system.

Phospholipids are typically identified by the trivial names of the acyl chains and the trivial name of the head group. The most common phospholipids are frequently abbreviated by four letter acronyms, di-myristoyl phosphatidyl choline may be abbreviated DMPC, while palmitoyl oleoyl phophatidyl ethanolamine may be abbreviated POPE. The trivial names of several fatty acid moieties are given below together with the IUPAC names of the unsaturated fatty acids moieties, which explicitly name the location and type of double bonds in the acyl chain.

| Saturated Acyl Chain | Trivial Name |
| --- | --- |
| 3:0 | Propionoyl |
| 4:0 | Butanoyl |
| 5:0 | Pentanoyl |
| 6:0 | Caproyl |
| 7:0 | Heptanoyl |
| 8:0 | Capryloyl |
| 9:0 | Nonanoyl |
| 10:0 | Capryl |
| 11:0 | Undecanoyl |
| 12:0 | Lauroyl |
| 13:0 | Tridecanoyl |
| 14:0 | Myristoyl |
| 15:0 | Pentadecanoyl |
| 16:0 | Palmitoyl |
| 16:0 [$(CH_3)_4$] | Phytanoyl |
| 17:0 | Heptadecanoyl |
| 18:0 | Stearoyl |
| 19:0 | Nonadecanoyl |
| 20:0 | Arachidoyl |

| Acyl Chain (chain length:# of double bonds) | Trivial Name | IUPAC Name |
| --- | --- | --- |
| 14:1 | Myristoleoyl | 9-cis-tetradecenoic |
| 14:1 | Myristelaidoyl | 9-trans-tetradecenoic |
| 16:1 | Palmitoleoyl | 9-cis-hexadecenoic |
| 16:1 | Palmitelaidoyl | 9-trans-hexadecenoic |
| 18:1 | Petroselinoyl | 6-cis-octadecenoic |
| 18:1 | Oleoyl | 9-cis-octadecenoic |
| 18:1 | Elaidoyl | 9-trans-octadecenoic |
| 18:2 | Linoleoyl | 9-cis-12-cis-octadecadienoic |
| 18:3 | Linolenoyl | 9-cis-12-cis-15-cisoctadecatrienoic |
| 20:1 | Eicosenoyl | 11-cis-eicosenoic |
| 20:4 | Arachidonoyl | 5,8,11,14(all-cis) eicosatetraenoic |
| 22:1 | Erucoyl | 13-cis-docosenoic |
| 22:6 | DHA | 4,7,10,13,16,19 (all-cis) docosahexaenoic |
| 24:1 | Nervonoyl | 15-cis-tetracosenoic |

Liposomes may be used in multilamellar vesicle form (MLV), large unilamellar vesicle form (LUV) having between about 500 nm and 50 nm diameters, preferably about 100 nm diameters, or as small unilamellar vesicles (SUV) having diameters of about 50 nm or less. 100 nm LUVs are desirable for a number of reasons. The distribution of $C_{60}$ is more homogeneous compared to a preparation containing MLVs. This size liposome can persist in circulation for longer because it will avoid uptake by the reticuloendothelial system, and 100 nm vesicles can escape the vasculature to reach interstitial space. Generally, preferred fullerene containing liposomes for pharmaceutical use will be principally in the range of 0.1 to 0.5 microns, with compositions comprising liposomes principally in the range 0.1 to 0.3 microns being more preferred.

Liposomes may be frozen or dried, for example by lyophilization to increase stability for longer term storage. Lipid preparations can be stabilized for freezing and drying by including carbohydrates in the composition. Stabilizing agents may be included in a fullerene containing liposome composition. Suitable agents include one or more sugars selected from the group consisting of glucose, sucrose, maltose, lactose, galactose, trehalose, and raffinose.

Many biological membranes carry a net negative charge on their surface. The charge is generally imparted by the presence of anionic phospholipid species in the membrane. The major naturally occurring anionic phospholipids are phosphatidylserine, phosphatidylinositol, phosphatidic acid, and cardiolipin. Some bacterial systems also contain phosphatidylglycerol. Having a charged surface can minimize the extent of liposome aggregation and model native membranes. Native brain tissue extracts can be modeled by a blend of unsaturated synthetic lipids (e.g., dioleoyl) in a ratio of about 5:3:2 (wt %), PE:PS:PC. This models the general phospholipid composition of most brain tissues.

Cholesterol is a membrane constituent widely found in biological systems which serves a unique purpose of modulating membrane fluidity, elasticity, and permeability. Cholesterol can fill in gaps created by imperfect packing of other lipid species when non-lipid molecules are embedded in the membrane.

The phase transition temperature Tc of a lipid is defined as the temperature required to induce a change in the lipid physical state from the ordered gel phase, where the hydrocarbon chains are fully extended and closely packed, to the disordered liquid crystalline phase, where the hydrocarbon chains are randomly oriented and fluid. There are several factors which directly affect the phase transition temperature including hydrocarbon length, unsaturation, charge, and headgroup species. As the hydrocarbon length is increased, van der Waals interactions become stronger requiring more energy to disrupt the ordered packing, thus the phase transition temperature increases. Likewise, introducing a cis double bond into the acyl group puts a kink in the chain which requires much lower temperatures to induce an ordered packing arrangement. Packing of headgroups can greatly influence Tc. The transition temperature of DMPE is 50° C. while the transition temperature of DMPC is 23° C. The PC head group is sterically larger than the PE head group.

| Lipids | Carbons:Unsaturation | Transition Temperature Tc (° C.) | Net Charge at pH 7.4 |
|---|---|---|---|
| DLPC | 12:0 | −1 | 0 |
| DMPC | 14:0 | 23 | 0 |
| DPPC | 16:0 | 41 | 0 |
| DSPC | 18:0 | 55 | 0 |
| DOPC | 18:1 | −20 | 0 |
| DMPE | 14:0 | 50 | 0 |
| DPPE | 16:0 | 63 | 0 |
| DOPE | 18:1 | −16 | 0 |
| DMPA.Na | 14:0 | 50 | −1.3 |
| DPPA.Na | 16:0 | 67 | −1.3 |
| DOPA.Na | 18:1 | −8 | −1.3 |
| DMPG.Na | 14:0 | 23 | −1 |
| DPPG.Na | 16:0 | 41 | −1 |
| DOPG.Na | 18:1 | −18 | −1 |
| DMPS.Na | 14:0 | 35 | −1 |
| DPPS.Na | 16:0 | 54 | −1 |
| DOPS.Na | 18:1 | −11 | −1 |

Phospholipids are not uniformly miscible with each other in binary mixtures. Differences in chain length and chain flexibility (such as resulting from cis-unsaturated bonds) can create voids in the lipid bilayer interior that are energetically unfavorable, resulting in segregation of lipid types and flat phase transition temperature curves. Mixtures of lipids with different head groups but similar chain compositions tend to be more miscible. The presence of fullerene molecules in the interior of the bilayer can alter the usual behavior by occupying voids, so that combinations of lipids that are not normally miscible may be surprisingly capable of incorporating and uniformly distributing fullerenes.

Neutral phospholipid head groups such as phosphatidyl choline and phosphatidyl ethanolamine are also strongly dipolar. These head groups possess an intrinsic charge separation with a negative charge appearing at the phosphate group and a positive charge centered at the nitrogen on the exposed end of the head group. The head groups typically do not lay horizontal in the plane of the lipid bilayer, but are rather tilted with the positive ends directed somewhat towards the water exposed surfaces. The degree of tilt and the electrostatic profile can be influenced by the composition of the head-group region of the bilayer. This combined with the local structure of water molecules, the glycerol backbone of the lipid and other structural factors results in an electrostatic charge profile in which there is a significant electrostatic voltage drop across the polar aqueous interface of the bilayer extending a few carbons into the non-polar acyl chain interior of the bilayer.

In addition, atoms in the lipid bilayer are more or less rigidly ordered as a function of position in the bilayer depending on several factors. Other things being equal, at temperatures above the liquid-crystal phase temperature, the rigidity of the atomic packing is highest among carbon atoms of the acyl chains near the level of the glycerol backbone. Closer to the ends of the acyl chains at the center of a bilayers, the carbon atoms are much less rigidly packed, approximating a fluid oil. At the polar aqueous interface of the bilayer, the degree of order is affected by how well the acyl chains are able to pack as well as the uniformity of the head groups and the degree of hydration associated with the head-groups that comprise the aqueous interface region.

Molecules that are incorporated into the lipid bilayer can interact with and be affected by the electrostatic profile and order profile of a lipid bilayer. $C_{60}$ is a symmetric molecule about 1 nm in diameter. The size and shape of fullerenes suggest a preference for less rigid, more fluid potions of the lipid bilayer. The use of mono-unsaturated lipids in liposomes can increase the relative degree of disorder at positions in the bilayer closer to the aqueous interface thereby potentially increasing the capacity of a lipid bilayer to accommodate fullerenes.

"Treating" or "treatment" of a disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease or condition, is sufficient to effect a desirable treatment for the disease or condition. The "therapeutically effective amount" will vary depending on the compound, the disease and its severity and the age, weight, etc., of the mammal to be treated. A "therapeutically effective amount" need not result in a complete cure, but may provide partial relief of one or more symptoms or retard the progression of a disease or condition.

Generally, the capacity of fullerene molecules to neutralize reactive molecules, such a free radicals and reactive oxygen species, means that compositions comprising fullerene molecules can be used to treat diseases and conditions in which reactive species and/or oxidative damage causes tissue damage. When incorporated into an effective delivery system, non-water soluble fullerene compositions may be used in such therapeutic applications. In particular, the fullerene containing liposome compositions may be used in methods to treat diseases or conditions associated with oxidative damage. Conditions include oxidative damage to skin, which may be treated by topically administering a therapeutically effective amount of a composition comprising non-water soluble fullerene, for example, liposomes comprising fullerene molecules, to the affected tissue. Alternatively, a composition comprising fullerene containing liposomes may be administered by any appropriate route to deliver the composition to tissues affected by oxidative damage or damage caused by reactive molecules.

Thus, liposome containing fullerenes such as are described herein can be used in a method of treatment of diseases caused by free radicals comprising administering a composition comprising non water soluble fullerenes or fullerene derivatives to an individual so as to neutralize free radicals within cell membranes. Fullerenes can be modified such that they neutralize very highly reactive radicals but do not interfere with less reactive radicals, for example by derivatizing the fullerene to reduce the affinity towards particular classes of reactive molecules. Preferably, the fullerenes include the synthetically modified fullerenes described above. The fullerenes may be derivatized with one or more lipophilic groups to enhance their ability to stably associate with lipid membranes. Liposomes comprising fullerenes may incorporate an amphiphilic moiety. The combination of a lipophilic moiety on one pole and a hydrophilic or amphiphilic moiety on the other pole can be used to position the fullerene in membranes at the water-lipid interface. A moiety that enhances their delivery to a specific target tissues can be chosen, for example the fullerene bearing liposomes may be targeted to endothelial cells, thrombi, or inflammatory cells by the use of targeting moieties specific for the target tissue.

A fullerene containing liposome composition may be administered in vivo by any suitable route including but not limited to: inoculation or injection (e.g., intravenous, intraperitoneal, intramuscular, subcutaneous, intra-aural, intra-articular, intra-mammary, and the like). A fullerene containing liposome composition may be incorporated into a broad range of materials including but not limited to gels, oils, emulsions and the like for administration as a topical therapeutic or incorporated into cosmetic formulations to provide an antioxidant capacity to the cosmetic formulation. Such uses include topical application (e.g., on areas such as eyes, skin, in ears or on afflictions such as wounds and burns), and by absorption through epithelial or mucocutaneous linings (e.g., nasal, buccal, vaginal, rectal, gastrointestinal mucosa, and the like).

Examples other various topical compositions include ointment, cream, lotion, moisturized patch or moisture-free patch, shampoo, gel, rinse, face lotion, milky lotion, paste, shaving cream, foundation, cologne, pack, semi-solid, solid or liquid. These preparations can be produced in accordance with routine methods, for example, as described below using, as necessary, antiseptics (including carboxylic acids such as dehydroacetic acid, salicylic acid and disodium edetate; and phenols such as ethyl paraoxybenzoate, methyl paraoxybenzoate, isopropyl paraoxybenzoate and thymol), wetting agents (including glycols such as glycerin, propylene glycol, dipropylene glycol and 1,3-butylene glycol; organic salts such as hyaluronic acid; and amides such as urea), consistency agents (including polymer compounds such as polyethylene glycol; and celluloses such as carboxymethyl cellulose sodium and carboxypropyl cellulose), buffers (including organic acids such as citric acid, lactic acid and tartaric acid; inorganic acids such as hydrochloric acid and boric acid; salts such as sodium dihydrogen phosphate and sodium citrate; organic bases such as triethanolamine; and inorganic bases such as sodium hydroxide and potassium hydroxide), adsorbents (including water-containing aluminum silicates such as kaolin and bentonite; and inorganic bases such as magnesium hydroxide-aluminum hydroxide co-precipitate and aluminum hydroxide), bases (including organic substances such as white petrolatum, Tween 60, Tween 80, liquid paraffin, beeswax, petrolatum, castor oil, silicone oil, hydrogenated castor oil, natural rubber, coconut oil fatty acid diethanolamide, polyoxyethylene hydrogenated castor oil, natural rubber latex and 1,3-pentadiene copolymer resin; polymer compounds such as polybutene, synthetic rubber SBR, polyethylene glycol monostearate, polyoxyethylene glycol monostearate, polyoxyethylene cetostearyl ether, polyoxyethylene oleylcetyl ether, silicon, starch grafted acrylate 300, sodium polyacrylate, methacrylic acid-n-butyl acrylate copolymer and carboxyvinyl polymer; fatty acids such as stearic acid; alcohols such as cetanol and myristyl alcohol, and fatty acid esters such as octadodecyl myristate, isopropyl myristate and cetyl octanoate), solvents (including carbohydrates such as ethanol, isopropanol, 1,3-butylene glycol, n-octadecylalcohol, crotamiton and caprylic/capric acid triglyceride), stabilizers (including inorganic salts such as sodium metaphosphate, zinc oxide and titanium oxide; and organic salts such as sodium polyoxyethylene lauryl sulfate ether sulfate and sodium lauryl sulfate), adhesives (including polymer compounds such as sodium polyacrylate and dipropylene glycol), emulsifiers (including carbohydrates such as sorbitan monooleate, polyoxyethylene sorbitan monooleate, D-sorbitol, polyglycerin monolaurate and sodium polyoxyethylene lauryl ether sulfate), surfactants (including polymer compounds such as polyglycerin monolaurate and polyoxyethylene oleyl alcohol ether), squalane, diluent, Span 60, Span 80, gelatin, propylparaben, methylparaben, lauryldimethyl-aminoacetate betaine, coconut oil fatty acid diethanol amide, N-[alkyl(12,14)oxy-2-hydroxypropyl]-L-arginine hydrochloride, silicone oil, jojoba oil, and fragrance.

Any fragrances can be used provided they can be generally used in foods, cosmetics, pharmaceuticals and so forth. Examples of naturally-derived fragrances include those obtained from plants such as rose, lavender and orange, and those obtained from animals such as musk oil (musk) obtained from musk deer and castorium (castor oil) obtained from beavers. Examples of synthetic fragrances include limonene, .beta.-caryophyllene, farnesol, citral, gamma.-undecalactone, indole and rilal.

Ointments are produced by, for example, heating and stirring an active ingredient and base, heating and dispersing, followed by cooling to the room temperature while stirring.

Creams are produced by, for example, first producing a base while heating and stirring, adding an active ingredient itself or a solution containing the active ingredient while heating and stirring, and cooling the resulting emulsion to the room temperature.

Lotions are produced by, for example, adding the active ingredient itself or a solution containing the active ingredient to an oily base or mixed base consisting of an oily base melted by heating and an aqueous base while stirring and heating, and then adding an aqueous base and cooling the resulting liquid to the room temperature.

Moisturized patches are produced by, for example, adding an additive to a mixed base consisting of an oily base melted by heating and an aqueous base while stirring, adding an active ingredient or a solution containing the active ingredient to the mixture while heating with stirring, rolling out the resulting paste onto a non-woven fabric and cutting to an appropriate size.

Moisture-free patches are produced by, for example, adding an active ingredient or a solution containing the active ingredient to a mixed base consisting of an oily base melted by heating while heating and stirring, adding this to a mixture of synthetic resin that has been melted by heating while stirring, rolling out the resulting paste onto a non-woven or woven fabric and cutting to an appropriate size.

Gels are produced by, for example, uniformly dissolving a gel base followed by adding a hydrophilic organic solvent, adding an active ingredient, heating, dissolving and dispersing. A solvent is then added thereto while heating. Next, after neutralizing while stirring, the mixture is cooled to the room temperature.

Shampoos are produced by, for example, heating purified water, adding an active ingredient, anionic surfactant, humectant and so forth, and cationic polymer as necessary, followed by uniformly dissolving and then cooling.

Pastes are produced by, for example, adding fats and oils to a wax, heating to melt, adding pigment, hydrocarbon and effective ingredient and so forth, and humectant as necessary, followed by mixing uniformly and cooling.

Rinses are produced by, for example, adding aqueous ingredients such as effective ingredient, humectant and cationic surfactant to purified water followed by melting with heating. Oily components such as higher alcohols and hydrocarbons are then added thereto after melting with heating followed by stirring to obtain a uniform mixture and then cooling.

Liquids are produced by, for example, adding and mixing an effective ingredient, humectant, lower alcohol and so forth to purified water, and then adding water-soluble polymer as necessary. Liquids can also be produced by adding these to mixture of oily components such as fatty acids, fats and oils and fatty acid esters as necessary followed by melting with heating.

Soap is produced by, for example, adding alkali to heated fats and oils. Alternatively, soap is produced by adding and stirring an added lower alcohol in fats and oils followed by the addition of alkali, purified water and humectant. Polysaccharides may also be added to this and mixed thoroughly followed by the addition of dye, fragrance and an effective ingredient followed by mixing uniformly, cooling and drying to obtain soap.

Milky lotions can be produced by, for example, adding an effective ingredient and humectant, etc. to purified water followed by heating to melt, adding this to oily components such as surfactant and higher alcohol that have been melted by heating, and then mixing uniformly and cooling.

Shaving creams can be produced by, for example, adding an active ingredient, humectant, alkali and so forth to purified water followed by heating and melting. This is then added to a mixture of necessary ingredients such as fatty acid, fatty acid esters, fats and oils and so forth that have been melted by heating followed by mixing uniformly and cooling.

Face lotions are produced by, for example, adding an active ingredient, thickener, humectant and so forth to purified water followed by the addition of a mixture of alcohol, surfactant and oily components such as fats and oils and mixing uniformly.

Foundations are produced by, for example, mixing pigments and coloring pigments of finely ground clay minerals, adding fatty acid, higher alcohols and other fats and oils and esters and mixing uniformly.

Colognes are produced by, for example, adding and mixing an effective ingredient, humectant, lower alcohol and so forth into purified water, adding water-soluble polymer as necessary and then adding fragrance after cooling. If necessary, colognes can also be produced by adding these to a mixture of oily ingredients such as fatty acids, fats and oils and fatty acid esters, etc. after melting by heating, and then adding fragrance after cooling.

The raw materials used in packs are completely different depending on the preparation form. If the pack is in the form of a jelly, it is produced by, for example, heating and melting an effective ingredient, humectant, alkali and so forth in purified water, adding thickener, water-soluble polymer and so forth, followed by stirring. Next, alcohols, surfactant and so forth are added and dissolved followed by cooling.

Further, in the production of topical compositions, other pharmaceutically effective ingredients may be contained therein in addition to the fullerene agents provided that they do not impair the effect of combining those agents which is dermatologically applicable. Examples of these pharmaceutically active ingredients include known refrigerants, keratolytics, cortical inhibitors, antiseborrheics, germicides, antipruritics as well as drugs that can be used for skin diseases, specific examples of which include menthol, salicylic acid, estradiol, glycyrrhizic acid, benzalkonium chloride, phenol and camphor; narcotics and antihypnotics such as ethylmorphine hydrochloride, oxycodone hydrochloride, cocaine hydrochloride, pethidine hydrochloride, methamphetamine hydrochloride, dl-methylephedrine hydrochloride, morphine hydrochloride, fentanyl citrate, levallorphan tartrate; local germicides such as povidone iodide and iodoform; enzyme preparations such as lysozyme hydrochloride, streptokinase, streptodornase trypsin and deoxyribonuclease; herbal medicines such as Lithospermi Radex extract and scopolia extract; hemorrhoid preparations such as non-viable *E. coli*, epidihydrocholesterin and tribenoside; and hemostyptics such as thrombin, cellulose oxide, and sodium alginate.

While the invention has been described in detail with reference to preferred embodiments thereof, it will be apparent to one skilled in the art that various changes can be made, and equivalents employed, without departing from the scope of the invention. The following examples are illustrative of the preparation and analysis of fullerene containing liposome compositions including favorable and comparative unfavorable results and should not be considered as limiting of the foregoing disclosure in any way.

EXAMPLES

Example 1

Amphiphilic compound 5 was synthesized using a modified diazo addition procedure originally reported by Diederich, Wudl and others (Diederich, F., Isaacs, L. and Philp, D., *J Chem Soc*, Perkin Trans 2:391, 1994; S. Shi, K. C. Khemani, Q., Li, and F. Wudl, *J. Am. Chem. Soc.* 114:10656, 1992). Diazomalonate 2 was prepared by reacting equal molar amounts of dodecylmalonate and p-toluenesulfonyl azide in the presence of triethyl amine (TEA) in benzene. Pure diazomalonate 2 was then reacted with fullerenes such as $C_{70}$ in refluxing toluene or xylene, the reaction mixture was purified with silica gel flash chromatography and the $C_{70}$ monoadduct 3 was characterized by NMR and MALDI-MS. Subsequently, monoadduct 3 was heated together in refluxing toluene with diazomalonate 1, which was synthesized in a similar manner to diazomalonate 2. The resulting $C_{70}$ bisadducts 4 were isolated from the reaction mixture via flash chromatographic separation method. In the final step, bisadduct 4 was dissolved (5 mg/mL) and stirred in a 1:1 mixture of dichloromethane (DCM) and trifluoroacetic acid (TFA) for 3 hours at room temperature. Upon completion of the reaction monitored by TLC, TFA and DCM were removed by a combination of aqueous extraction and rotavap. The final product 5 was obtained in pure form as demonstrated by NMR and MALDI-MS. Other compounds 6-11 were also prepared in a similar manner.

Compound 5 was formulated in liposomes made of lecithin purified from egg yolks by the reverse phase method. See, e.g., U.S. Pat. No. 4,522,803. Briefly, one part amphipathic $C_{70}$ malonate was added to two parts lecithin in diethyl ether. To this mixture an aqueous buffered solution was added and the organic solvent was removed by sparging. The resultant liposomes were homogeneous as viewed in a light microscope. Surprisingly, the amphipathic fullerene liposomes were dimensionally stable. When said liposomes were extruded through channels of a uniform diameter, for example through a nuclepore membrane, the amphipathic fullerene surprisingly did not separate from the phospholipids. This was determined by buoyant density separation under conditions where the fullerene would form a precipitate upon centrifugation were it not stably associated with the lipids. The observation that the amphipathic fullerene remained associated with the phospholipids during and after severe mechanical distortion is an indication that the two species are sterically compatible. When these amphiphilic fullerene liposomes were administered to animals they were effective in blocking two different inflammatory responses.

Example 2

Contact hypersensitivity by phorbol myristic acetate (PMA) is a well-known model for studying cutaneous inflammatory response. Exposure leads to an increase in mitotic cells, thickening, capillary leak and infiltration of lymphocytes. Segal et al., "Identification of phorbolol myrisate acetate as a new metabolite of phorbol myristate acetate in mouse skin;" Canc. Res., 35:2154-59, 1975. Keratinocytes respond to chemical irritation by producing TNF-α, Interleukins 1 and 6, growth factors and chemoattractants for neutrophils and, later, macrophages. The reaction is blocked by anti-inflammatory drugs such as glucocorticoids, indomethacin and cyclosporin. Pugnero & Queralt "Effect of topically applied cyclsporin A on arachidonic acid (AA) and tetradecanoylphorbol (TPA) induced dermal inflammation on mouse ear;" Inflammation, 21: 357-69, 1997. The aforementioned liposome formulation of the amphipathic fullerene was effective in blocking PMA hypersensitivity reaction in mice. In this same experiment, the water soluble fullerene C3 had no effect. This comparison shows the membrane-targeted $C_{70}$ adduct is more effective.

Example 3

Pruritis. Substance P is a neurotransmitter which selectively excites cutaneous dendritic cells to stimulate the specific neurons responsible for the itch response. In mice the pathway for this response is via the arachidonic acid cascade mediated through leukotriene B4. Andoh et al., "Involvement of leukotriene B(4) in substance P-induced itch-associated response in mice;" J. Investigat. Derm., 117:1621-26, 2001. The aforementioned liposome formulation of the amphipathic fullerene completely blocked this cell-mediated pathway, as measured by the frequency at which mice scratch themselves after treatment.

Example 4

Compound 5 was dissolved in ethyl ether to which egg phosphatidyl choline was added in an amount to make a 1:1 molar ratio. In a second vial, no phospholipid was added. Next, an aqueous buffer solution was added to each. The two phase mixture was sonicated in a bath sonicator while sparging with nitrogen gas. After the ether was evaporated the resultant aggregates were amorphous. Examination in the microscope confirmed the compound in the absence of lipids did not form vesicles, rather was collected in disordered particles that stuck to the walls of the flask. The material formulated with phospholipid did not stick to the vessel walls. Examination in the microscope showed highly irregular shaped granules. An aliquot was carefully layered onto a 40% sucrose cushion and exposed to 18,000 G centrifugation for 30 min. Under these conditions, liposomes will buoy on top of the cushion because of their low density. In this experiment roughly half the substance was in the pellet, while the other half was on top of the sucrose cushion. This result indicated the fullerene adduct could not form vesicles at this low lipid: fullerene ratio. Rather, some fullerene adduct collected sufficient phospholipid to form vesicles, while the rest aggregated. Thus, unlike the amphiphilic fullerene described by Hirsch, the amphiphilic fullerenes described herein cannot form vesicles spontaneously or at low lipid ratios.

Example 5

Compound 15 is made using the scheme illustrated in FIG. 9. Following the method of Nakamura, 100 mg of $C_{70}$ in ODCB/THF mixture is reacted with 5 eq Grignard reagent prepared from Br—$(CH_2)_3$OTBDMS. See M. Sawamura, H. Iikura, E. Nakamura, J. Am. Chem. Soc. 118:12850, 1996); M. Sawamura, H. Iikura, T. Ohama, U. E. Hackler, E. Nakamura, Journal of Organometallic Chemistry, 599:32-36, 2000. After work-up and column purification compound 12 is produced in good yield. Compound 12 is reacted with bis-malonate 13 in toluene in the presence of DBU/$I_2$ to give adduct 14. After purification by chromatography, compound 14 is deprotected (HCl or TFA) to give compound 15.

Example 6

Figure 10:
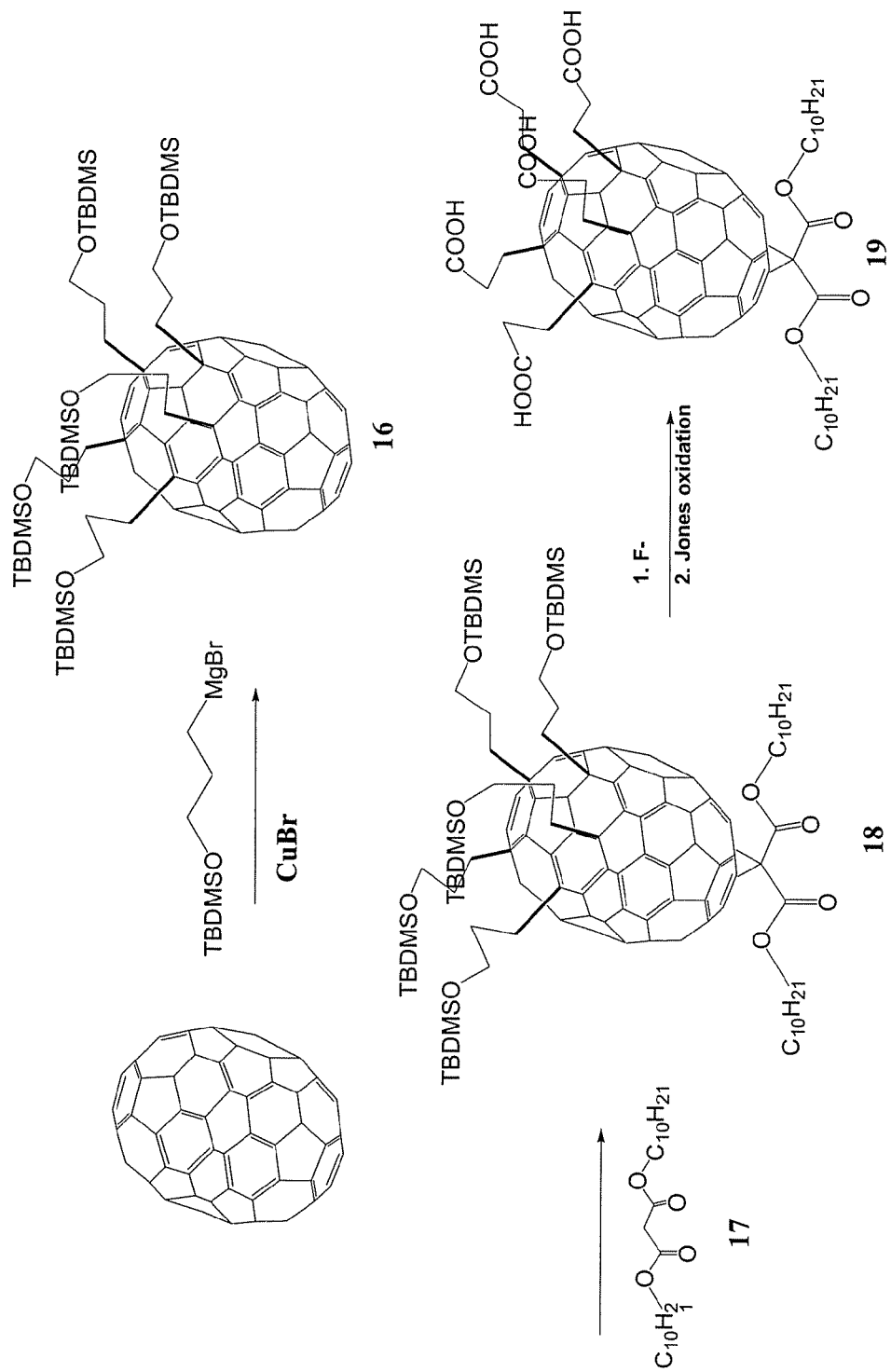

Compound 19 is made using the scheme illustrated in FIG. 10. Following the method of Nakamura, 100 mg of C70 in ODCB/THF mixture is reacted with 5 eq Grignard reagent prepared from Br—$(CH_2)_9CH_3$. After work-up and column purification compound 16 is produce in good yield. Compound 16 is reacted with malonate 17 to give bis-adduction 18 which can be isolated in good yield by column chromatography. Compound 18 is deprotected to the pentaol, which can be oxidized to the carboxylica acid 19 with chromic acid.

Example 7

Figure 11:
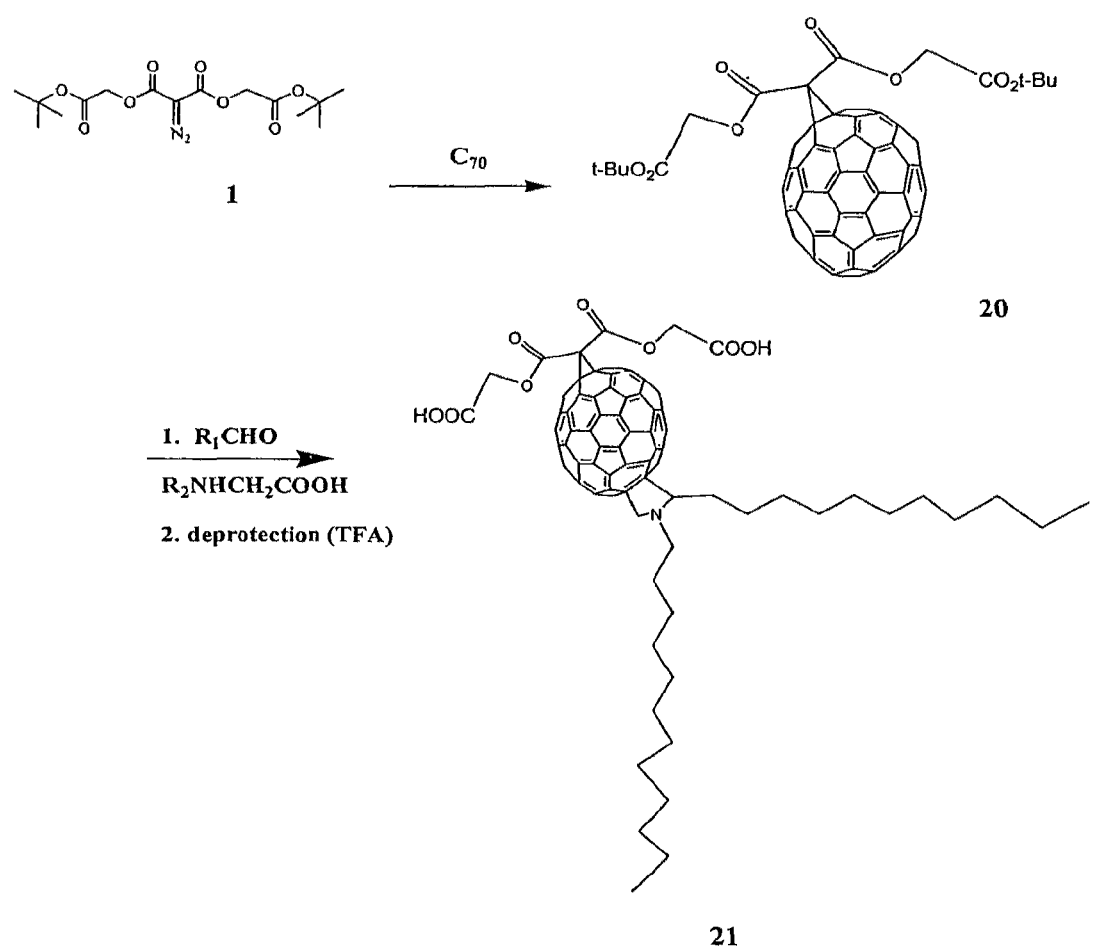
FIG. 11 illustrates preparation of compound 21.

Amphiphilic compound 21 is synthesized using a Prato reaction as illustrated in FIG. 11. Pure diazomalonate 1-prepared by methods discussed in Example 1 above—is reacted with fullerenes $C_{70}$ in refluxing toluene or xylene. When complete, the reaction mixture is purified with silica gel flash chromatography and the $C_{70}$ monoadduct 20 was characterized by NMR and MALDI-MS. Subsequently, monoadduct 20 was heated together in refluxing toluene or xylene with a 20-fold excess of dodecyl aldehyde and N-decyl glycine to give the fulleropyrrolidine addition product. After chromatographic purification, the diester was deprotected with TFA to give amphiphilic diacid 21 which could be characterized by NMR and MALDI mass spectroscopy.

What is claimed is:

1. A synthetically modified fullerene molecule having the formula

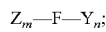

wherein F is fullerene of formula $C_p$, the fullerene having two opposing poles and an equatorial region;
Z and Y are positioned near respective opposite poles of $C_p$;
m=1-5 and Z is a hydrophilic chemical moiety;
n=1-5 and Y is a lipophilic chemical moiety;
p=60-120 and p is an even number.

2. The synthetically modified fullerene of claim 1, wherein each chemical moiety Z is composed of formula $A_rB$ in which A is a hydrophilic chemical moiety, r=1-4, and B is a chemical linker connecting said A to the fullerene, and each chemical moiety Y is composed of formula $DE_v$ in which E is a lipophilic chemical moiety and, v=1-4, and D is a chemical linker connecting the lipophilic chemical moiety to the fullerene.

3. The synthetically modified fullerene of claim 1, wherein F is a prolate ellipsoid shaped fullerene having a major axis and said poles are located at opposing ends of the major axis of the prolate ellipsoid fullerene.

4. The synthetically modified fullerene of claim 1, wherein Z and Y are configured such that when the molecule is contacted with a lipid bilayer in an aqueous medium, the equatorial region of F is selectively located within or in close proximity to the bilayer.

5. The synthetically modified fullerene of claim 2, wherein Z and Y are configured such that when the molecule is contacted with a lipid bilayer in an aqueous medium, the equatorial region of F is selectively located within or in close proximity to the bilayer.

6. The synthetically modified fullerene of claim 1, wherein the molecule in an extended configuration has an aspect ratio of about 2.1 to 15, and a diameter less than about 2 nm.

7. The synthetically modified fullerene of claim 2, wherein the molecule in an extended configuration has an aspect ratio of about 2.1 to 15, and a diameter less than about 2 nm.

8. The synthetically modified fullerene of claim 1, wherein p=60.

9. The synthetically modified fullerene of claim 1, wherein p=70.

10. A therapeutic or cosmetic composition comprising the synthetically modified fullerene of claim 1 uniformly dispersed within phospholipid bilayers.

11. A composition of claim 10, in which the molar ratio of fullerene to phospholipid is from about 1:10 to 1:2.

12. A topical composition in the form of a ointment, cream, lotion, moisturized patch or moisture-free patch, shampoo, gel, rinse, face lotion, milky lotion, paste, shaving cream, foundation, cologne, or pack comprising a synthetically modified fullerene according to claim 1.

13. A synthetic fullerene molecule having the formula $Z(C_{70})Y$; wherein Y is a lipophilic moiety covalently connected to $C_{70}$, optionally through a linking group, near a pole thereof, and wherein Z is a hydrophilic moiety covalently connected to $C_{70}$, optionally through a linking group, at or near a pole opposite to said Y; and, wherein said lipophilic moiety Y is capable of anchoring the synthetic fullerene molecule to a lipid membrane.

14. A composition comprising a plurality of synthetic fullerene molecules according to claim 13 uniformly dispersed in phospholipids.

15. A topical composition in the form of a ointment, cream, lotion, moisturized patch or moisture-free patch, shampoo, gel, rinse, face lotion, milky lotion, paste, shaving cream, foundation, cologne, or pack comprising a synthetic fullerene molecule according to claim 13.

16. A composition comprising in a pharmaceutically acceptable medium, a synthetic fullerene molecule according to claim 13 and another pharmaceutical molecule.

17. The composition of claim 16, wherein the pharmaceutical molecule is insulin.

* * * * *